US009532788B2

(12) United States Patent
Jordan et al.

(10) Patent No.: US 9,532,788 B2
(45) Date of Patent: Jan. 3, 2017

(54) SYSTEMS AND METHODS FOR DETERMINING THE MECHANICAL AXIS OF A FEMUR

(71) Applicant: Smith & Nephew, Inc., Memphis, TN (US)

(72) Inventors: Jason Sean Jordan, Hernando, MS (US); Michael Dean Hughes, Cordova, TN (US); Mark Ellsworth Nadzadi, Memphis, TN (US); Brian William McKinnon, Bartlett, TN (US); Paul Charles Crabtree, Jr., Nesbit, MS (US); David Timothy Mehl, Memphis, TN (US)

(73) Assignee: Smith & Nephew, Inc., Memphis, TN (US)

( * ) Notice: Subject to any disclaimer, the term of this patent is extended or adjusted under 35 U.S.C. 154(b) by 0 days.

(21) Appl. No.: 14/709,722

(22) Filed: May 12, 2015

(65) Prior Publication Data
US 2015/0238273 A1    Aug. 27, 2015

Related U.S. Application Data

(63) Continuation of application No. 14/223,400, filed on Mar. 24, 2014, now Pat. No. 9,101,393, which is a
(Continued)

(51) Int. Cl.
*A61B 17/15* (2006.01)
*A61B 17/56* (2006.01)
*A61B 17/17* (2006.01)

(52) U.S. Cl.
CPC ............. *A61B 17/15* (2013.01); *A61B 17/154* (2013.01); *A61B 17/155* (2013.01);
(Continued)

(58) Field of Classification Search
CPC ..... A61B 17/00; A61B 17/155; A61B 17/157; A61B 17/1703; A61B 17/1764; A61B 17/56; A61B 19/50; A61B 2019/502; A61B 2019/508; A61B 17/15; A61B 17/154
See application file for complete search history.

(56) References Cited

U.S. PATENT DOCUMENTS 4,528,980 A    7/1985   Kenna
4,633,862 A    1/1987   Petersen
(Continued)

FOREIGN PATENT DOCUMENTS

CN    1913844 A    2/2007
GB    2447702 A    9/2008
(Continued)

OTHER PUBLICATIONS

International Preliminary Report on Patentability for International Application No. PCT/US2011/040042, mailed Dec. 27, 2012.
(Continued)

*Primary Examiner* — Larry E Waggle, Jr.
(74) *Attorney, Agent, or Firm* — Fish & Richardson P.C.

(57) ABSTRACT

A method positions a profile of a prosthetic component on the three-dimensional model of a limb. Patient-specific anatomical data of the limb is gathered. First and second anatomical landmarks are identified to determine a first spatial relationship. A third anatomical landmark is identified to determine a second spatial relationship with respect to the first spatial relationship. The profile of the prosthetic component is positioned in all but one degree of freedom. A fourth anatomical landmark is identified to position the profile of the prosthetic component in the one remaining degree of freedom.

24 Claims, 25 Drawing Sheets

Related U.S. Application Data continuation of application No. 12/746,272, filed as application No. PCT/US2008/085897 on Dec. 8, 2008, now Pat. No. 8,702,712.

(60) Provisional application No. 60/992,977, filed on Dec. 6, 2007.

(52) U.S. Cl.
CPC ........ *A61B 17/157* (2013.01); *A61B 17/1703* (2013.01); *A61B 17/1725* (2013.01); *A61B 17/1764* (2013.01); *A61B 17/56* (2013.01); *A61B 2034/102* (2016.02)

(56) References Cited

U.S. PATENT DOCUMENTS

| | | | |
|---|---|---|---|
| 5,129,908 | A | 7/1992 | Petersen |
| 5,234,433 | A | 8/1993 | Bert et al. |
| 5,299,893 | A | 4/1994 | Salyer et al. |
| 5,320,529 | A | 6/1994 | Pompa |
| 5,380,332 | A | 1/1995 | Ferrante |
| 5,425,368 | A | 6/1995 | Brandt |
| 5,575,793 | A | 11/1996 | Carls et al. |
| 5,682,886 | A | 11/1997 | Delp et al. |
| 5,709,689 | A | 1/1998 | Ferrante et al. |
| 5,798,924 | A | 8/1998 | Eufinger et al. |
| 5,951,605 | A | 9/1999 | Dennis et al. |
| 6,205,411 | B1 | 3/2001 | DiGioia, III et al. |
| 6,327,491 | B1 | 12/2001 | Franklin et al. |
| 6,423,077 | B2 | 7/2002 | Carol et al. |
| 6,529,762 | B1 | 3/2003 | Ladebeck |
| 6,558,421 | B1 | 5/2003 | Fell et al. |
| 6,768,486 | B1 | 7/2004 | Szabo et al. |
| 6,928,742 | B2* | 8/2005 | Broers .................. A61B 5/103 33/227 |
| 7,220,267 | B2 | 5/2007 | Jones |
| 7,427,200 | B2 | 9/2008 | Noble et al. |
| 7,534,263 | B2 | 5/2009 | Burdulis, Jr. et al. |
| 7,618,451 | B2 | 11/2009 | Berez et al. |
| 8,425,524 | B2 | 4/2013 | Aker et al. |
| 8,702,712 | B2* | 4/2014 | Jordan ................. A61B 17/155 606/86 R |
| 2001/0001120 | A1 | 5/2001 | Masini |
| 2002/0055783 | A1 | 5/2002 | Tallarida et al. |
| 2002/0115934 | A1 | 8/2002 | Tuke |
| 2002/0180760 | A1 | 12/2002 | Rubbert et al. |
| 2003/0000535 | A1 | 1/2003 | Galloway, Jr. et al. |
| 2003/0045885 | A1 | 3/2003 | Margulies et al. |
| 2003/0060890 | A1 | 3/2003 | Tarabishy |
| 2003/0078587 | A1 | 4/2003 | Lechot et al. |
| 2003/0163137 | A1 | 8/2003 | Smucker et al. |
| 2004/0030245 | A1 | 2/2004 | Noble et al. |
| 2004/0153079 | A1 | 8/2004 | Tsougarakis et al. |
| 2004/0260301 | A1 | 12/2004 | Lionberger et al. |
| 2005/0075649 | A1 | 4/2005 | Bova et al. |
| 2005/0148843 | A1 | 7/2005 | Roose |
| 2006/0142657 | A1 | 6/2006 | Quaid et al. |
| 2006/0161051 | A1 | 7/2006 | Terrill-Grisoni et al. |
| 2006/0276786 | A1 | 12/2006 | Brinker |
| 2007/0106299 | A1 | 5/2007 | Manspeizer |
| 2007/0123912 | A1 | 5/2007 | Carson |
| 2007/0198022 | A1 | 8/2007 | Lang et al. |
| 2007/0219639 | A1 | 9/2007 | Otto et al. |
| 2007/0270680 | A1* | 11/2007 | Sheffer .................. A61B 90/36 600/407 |
| 2007/0276224 | A1 | 11/2007 | Lang et al. |
| 2008/0009952 | A1 | 1/2008 | Hodge |
| 2008/0097450 | A1 | 4/2008 | Brown et al. |
| 2008/0154269 | A1 | 6/2008 | Roger et al. |
| 2008/0171932 | A1 | 7/2008 | Yan et al. |
| 2008/0188855 | A1 | 8/2008 | Brown et al. |
| 2008/0242953 | A1 | 10/2008 | Dew et al. |
| 2008/0243127 | A1 | 10/2008 | Lang et al. |
| 2008/0312663 | A1 | 12/2008 | Haimerl et al. |
| 2008/0319448 | A1 | 12/2008 | Lavallee et al. |
| 2008/0319491 | A1 | 12/2008 | Schoenefeld |
| 2009/0087276 | A1* | 4/2009 | Rose .................... A61B 17/155 409/79 |
| 2009/0088753 | A1 | 4/2009 | Aram et al. |
| 2009/0088755 | A1 | 4/2009 | Aker et al. |
| 2009/0088763 | A1 | 4/2009 | Aram et al. |
| 2009/0093816 | A1 | 4/2009 | Roose et al. |
| 2009/0138020 | A1 | 5/2009 | Park et al. |
| 2009/0157083 | A1 | 6/2009 | Park et al. |
| 2009/0163922 | A1 | 6/2009 | Meridew et al. |
| 2009/0171184 | A1 | 7/2009 | Jenkins et al. |
| 2009/0227905 | A1 | 9/2009 | Warkentine et al. |
| 2009/0270868 | A1 | 10/2009 | Park et al. |
| 2009/0281415 | A1 | 11/2009 | Cupps et al. |
| 2009/0318976 | A1 | 12/2009 | Gabriel et al. |
| 2010/0023015 | A1 | 1/2010 | Park |
| 2010/0030223 | A1 | 2/2010 | Keller |
| 2010/0030231 | A1 | 2/2010 | Revie et al. |
| 2010/0076563 | A1 | 3/2010 | Otto et al. |
| 2010/0185202 | A1 | 7/2010 | Lester et al. |
| 2011/0202060 | A1 | 8/2011 | White et al. |

FOREIGN PATENT DOCUMENTS

| | | |
|---|---|---|
| WO | WO9325157 A1 | 12/1993 |
| WO | WO9400056 A1 | 1/1994 |
| WO | WO9625114 A1 | 8/1996 |
| WO | WO2004078078 A1 | 9/2004 |
| WO | WO2006078236 A1 | 7/2006 |
| WO | WO2006129087 A1 | 12/2006 |
| WO | WO2009001083 A1 | 12/2008 |
| WO | WO2009075562 A1 | 6/2009 |
| WO | WO2009106816 A1 | 9/2009 |
| WO | WO2010099231 A2 | 9/2010 |

OTHER PUBLICATIONS

International Search Report and Written Opinion for International Application No. PCT/US2011/040031, mailed Feb. 17, 2012.
International Preliminary Report on Patentability for International Application No. PCT/US2011/040031, mailed Dec. 27, 2012.
Office Action for Chinese Application 201180039329.3, mailed Oct. 10, 2014.
International Search Report and Written Opinion for International Application No. PCT/US2011/040042, mailed Feb. 17, 2012.
Office Action for U.S. Appl. No. 13/158,200, mailed Mar. 12, 2014.
International Search Report for International Application No. PCT/US2012/040373, mailed Oct. 23, 2012.
Visionaire Patient Matched Instrumentation—A technology from Smith & Nephew Design Rationale, 7 pages (2008).
Office Action for U.S. Appl. No. 12/746,272, mailed Jun. 18, 2013.
International Search Report for International Application No. PCT/US2011/047897, mailed Mar. 27, 2012.
International Search Report for International Application No. PCT/US2011/047860, mailed Mar. 19, 2012.
International Search Report for International Application No. PCT/US2011/047936, mailed Mar. 26, 2012.
International Search Report for International Application No. PCT/US201/047671, mailed Mar. 28, 2012.
International Search Report for International Application No. PCT/US2011/047675, mailed Feb. 29, 2012.
International Search Report for International Application No. PCT/US2011/047674, mailed Mar. 5, 2012.
International Preliminary Report on Patentability for International Application No. PCT/US2011/047674, mailed Feb. 19, 2013.
International Search Report for International Application No. PCT/US2011/047670, mailed Mar. 19, 2012.
International Preliminary Report on Patentability for International Application No. PCT/US2011/047670, mailed Feb. 19, 2013.
International Search Report for International Application No. PCT/US2011/056380, mailed May 21, 2012.
International Preliminary Report on Patentability for International Application No. PCT/US2011/056380, mailed Apr. 16, 2013.

(56) References Cited

OTHER PUBLICATIONS

International Search Report for International Application No. PCT/US2011/085897, mailed May 28, 2009.
International Preliminary Report on Patentability for International Application No. PCT/US2011/085897, mailed Jun. 8, 2010.
Office Action for U.S. Appl. No. 12/770,532 mailed Oct. 9, 2012.
Office Action for U.S. Appl. No. 12/770,532, mailed May 23, 2013.
Office Action for U.S. Appl. No. 13/157,991, mailed Jan. 15, 2014.
Office Action for U.S. Appl. No. 13/158,200, mailed Sep. 5, 2014.
"S-ROM® Noiles™ Rotating Hinge: Surgical Technique and Reference Guide," © 2002 DePuy Orthopaedics, Inc.
Extended European Search Report for European Application No. 08859728.1, mailed Oct. 11, 2013.
Patent Examination Report No. 1 for Australian Application No. 2011265254, mailed May 18, 2015.
Third Office Action for Chinese Application 200880119388, mailed Nov. 4, 2015.

\* cited by examiner

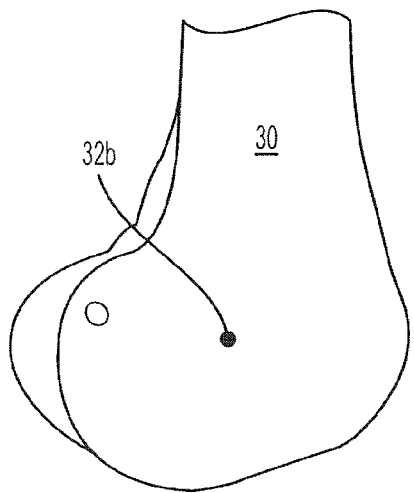
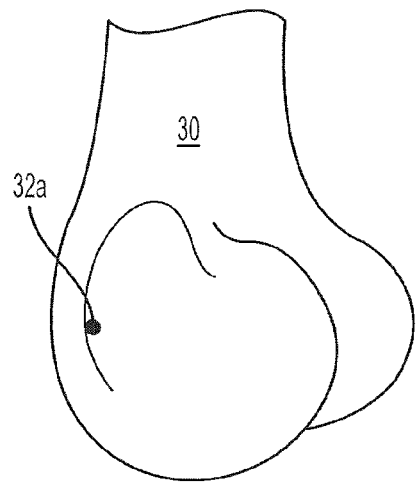
FIGURE 6a.     FIGURE 6b.
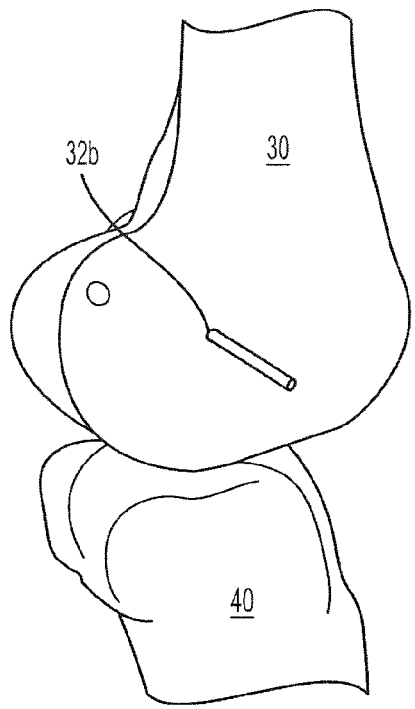
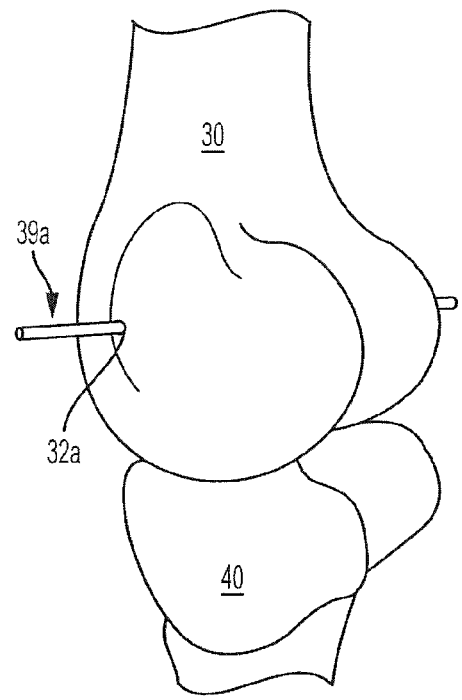
FIGURE 7a.     FIGURE 7b.

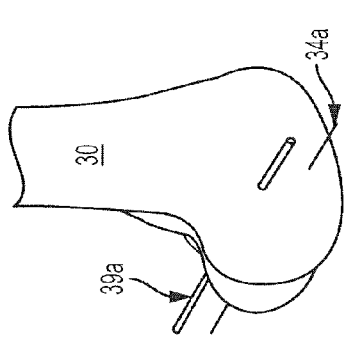
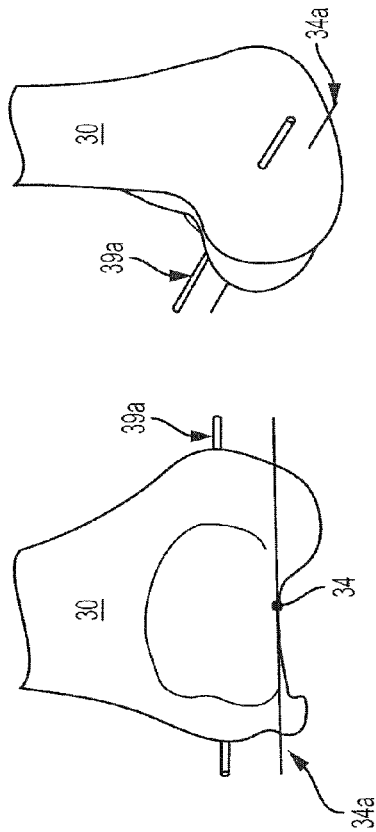
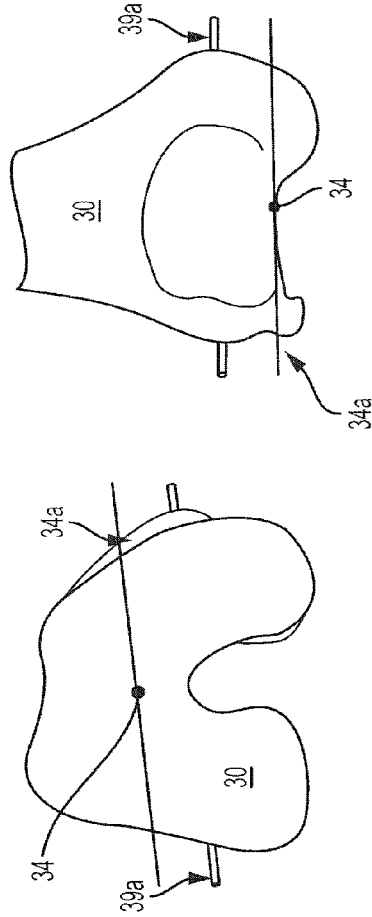
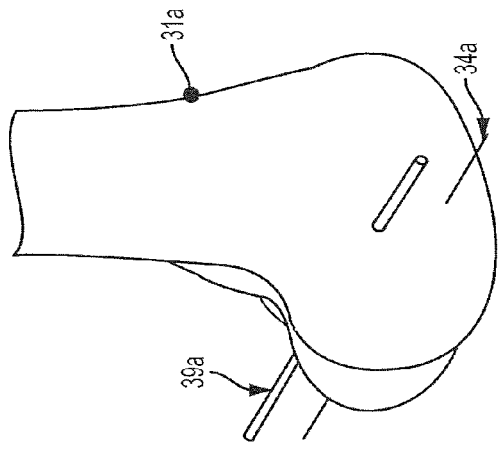
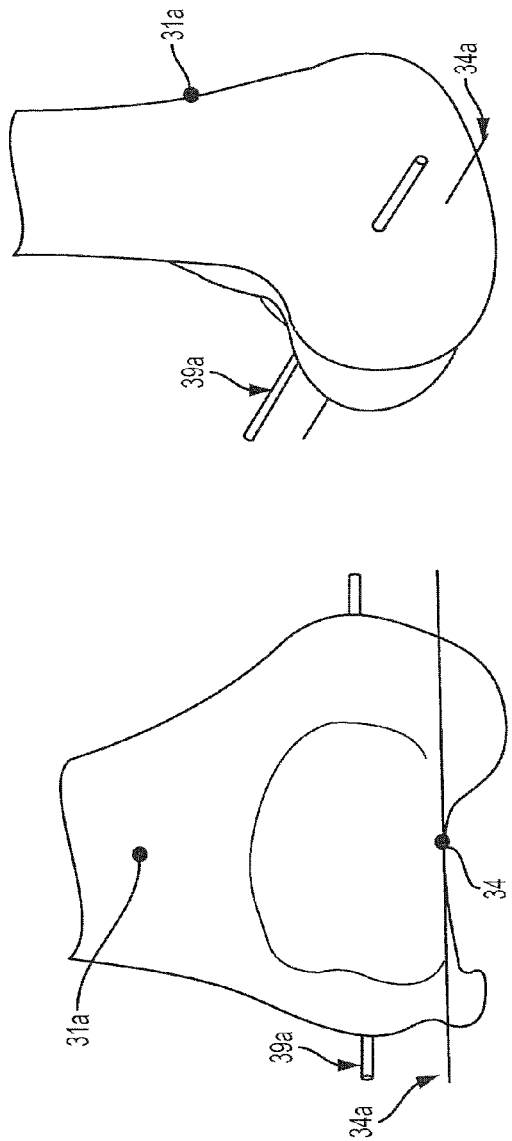

SYSTEMS AND METHODS FOR DETERMINING THE MECHANICAL AXIS OF A FEMUR

CROSS-REFERENCE TO RELATED APPLICATIONS

This application is a continuation of U.S. patent application Ser. No. 14/223,400, filed Mar. 24, 2014, now allowed, which is a continuation of U.S. patent application Ser. No. 12/746,272, filed Aug. 23, 2010, now U.S. Pat. No. 8,702, 712, issued Apr. 22, 2014, which is a national stage application of PCT/US2008/085897, filed Dec. 8, 2008, which claims the benefit of U.S. Provisional Application No. 60/992,977, filed Dec. 6, 2007. The disclosures of each of the prior applications are incorporated by reference in their entirety.

BACKGROUND OF THE INVENTION

1. Field

The present method relates generally to methods of determining the mechanical axis of a patient's limb using anatomical information and more particularly, to methods of providing a customized surgical device configured to guide a cutting tool along a plane perpendicular to the true, three-dimensional mechanical axis of a patient's limb.

2. Related Art

The mechanical axis of the human leg in the frontal plane is defined as a line drawn from the centre of the femoral head to the centre of the ankle joint. In a frontal plane, it normally passes just medial to the centre of the knee joint in the frontal plane. This line assumes sphericity in the femoral head and normal anatomy in the subtalar complex. In a sagittal plane, the normal mechanical axis runs from the centre of gravity, to the centre of the ankle joint. It therefore, runs just behind the femoral head (because the femoral neck is generally anteverted about 15°) and just in front of the knee.

FIG. 1 illustrates the mechanical axis of a deficient lower limb and a normal lower limb. FIG. 1a illustrates a deficient lower limb, wherein a gross malalignment (12) between the femoral (14) and tibial (16) mechanical axes is visible. The mechanical axis of the limb (18) does not pass through the centre of the knee joint (20) as it should. FIG. 1b illustrates a normal lower limb, wherein the femoral (14) and tibial (16) mechanical axes are generally aligned and pass through the centre of the knee joint (20). The transverse axis (22) is aligned with the distal femoral contact points and is generally perpendicular to the femoral and tibial mechanical axes (14, 16). The mechanical axis is generally aligned with the femoral (14) and tibial (16) mechanical axes.

It has generally been convention to design standard knee prosthetics to accommodate a wide variety of people within a population. However, not all patients fall within this population subset, nor can all patients achieve the same performance with a universal or standard implant. In one instance, a patient may have a severe varus or valgus deformity, dwarf condyle(s), excessive femoral bowing, or bony tumour(s) present. In another instance, a patient may have abnormally small or large bone structure. In these circumstances, a custom implant may be desirable to a surgeon. However, current methods of manufacturing custom implants are generally expensive, require specialized input from a surgeon, and are time-consuming procedures.

Medical devices, in particular femoral cutting blocks, have been used to prepare the distal portions of a femur in total knee arthroplasties (TKA's). Such cutting blocks are typically mounted to the femur after at least a first resection has been made, said at least first resection being facilitated by an adjustable instrument referenced by and extending from an intramedullary or extramedulary rod. The instruments are made adjustable so that they may be used universally between patients. While there are many benefits to adjustable instruments, there are also many disadvantages. Some disadvantages include increased overhead, bulky kits and containers, unnecessary or redundant instruments, large numbers of trials and different sizes, increased OR time, increased sterilization time between surgeries, and increased financial risk s to orthopaedic manufacturers which keep large numbers of assets on consignment.

Recent attempts have been made to streamline the surgical process and avoid the aforementioned disadvantages of standard resection instruments. Such methods have employed customized cutting blocks formed using anatomical information derived from a partial CT/MRI scan of a patient's knee joint. Corporations like OtisMed Corp. and ConforMIS, Inc. utilize such methods. However, to this end, it is believed that conventional customized cutting blocks and methods of distal femoral resection associated therewith do not ensure that at least one bony resection is made perpendicular to the true, three-dimensional mechanical axis of a patient. Instead, it is believed that the prior art approximates the mechanical axis by extrapolating a fixed number of degrees from the small anatomical axis portion visible in a partial scan of the knee joint.

For instance, if a partial knee CT scan or X-ray of a patient indicates a pre-operative anatomical axis at or around seven degrees, a conventional custom cutting block of the prior art will generally be formed to provide a distal femoral resection perpendicular to an axis displaced medially from said anatomical axis by a specified angle or number of degrees relative to the joint centre. The specified angle or number of degrees is believed to be chosen to reflect the mean deviation between anatomical and mechanical axes for a large population set. Said mean deviation has been generally accepted within the medical field as approximately 5-6 degrees. Therefore, using this methodology of the prior art, the mechanical axis in the example above would be approximated as being 1 degree from vertical, or about "seven degrees minus six degrees". It is believed that practicing this method does not accurately place femoral resections perpendicular to the true mechanical axis, since the relationship between anatomical axis and mechanical axis may greatly differ between patients. Furthermore, if there are any unnoticed deformities of the distal tibia or proximal femur present, such assumptions could carry gross consequences. Lastly, since the true mechanical axis is defined in three dimensions, simply rotating a resection plane medially a predetermined number of degrees from the anatomical axis in a coronal plane without adjusting for anterior-posterior slope in a sagittal plane would not place said resection plane perpendicular to the true, three-dimensional mechanical axis.

While it is generally accepted that for a majority of people, the mechanical axis of a lower limb averages five to six degrees medially from the anatomical axis of the femur, and that the intersection of the femoral and tibial mechanical axes at the knee subtend an average of 1.3 degrees varus (±2 degrees) and intersect just medial to the centre of the joint, these observations cannot be relied upon as fact or used in any sort of algorithm in determining proper resection. In fact, it has been determined through research that such relationships between anatomical axis and mechanical axis of the femur may range from 2-11 degrees.

Thus, benefits may exist in ascertaining the true, three-dimensional mechanical axis of a limb prior to surgery, to determine the best placement of a surgical device.

SUMMARY OF THE INVENTION

According to some embodiments, there is provided a method of determining the true, three-dimensional mechanical axis of a patient's limb using patient-specific anatomical information. The method includes the steps of: gathering patient-specific anatomical data of said limb using radiological or other conventional means; identifying first and second anatomical landmarks to determine a first spatial relationship; identifying a third anatomical landmark to determine a second spatial relationship with respect to said first spatial relationship; using said first and second spatial relationships to position a prosthetic component in all but one degree of freedom; and, identifying a fourth anatomical landmark to position said prosthetic component in said one remaining degree of freedom.

According to other embodiments, there is provided a cost-efficient method of determining the true mechanical axis of a patient's limb using non-invasive means. The method includes the steps of: gathering patient-specific anatomical data of said limb using radiological or other conventional means from at least two of a proximal limb portion, a central limb portion, and a distal limb portion; and, using said patient-specific anatomical data to determine the true, three-dimensional mechanical axis of said limb portion; wherein said anatomical data may be gathered in various states of flexion, extension, rotation (e.g., internal/external), subluxation (e.g., dislocation), and/or abduction/adduction (e.g., varus/valgus, pro-/supination); and, wherein said anatomical data is used to design a custom medical device.

According to yet other embodiments, there is provided a method of providing a customized surgical device. The method includes the steps of: gathering patient-specific anatomical data of said limb using radiological or other conventional means; using said patient-specific anatomical data to determine the true, three-dimensional mechanical axis of said limb portion; and providing a customized medical device capable of guiding a cutting tool in a plane transverse to said true, three-dimensional mechanical axis of a patient.

According to yet even other embodiments, there is provided a method of implanting a prosthetic device for a limb. The method includes the steps of: gathering patient-specific anatomical data of said limb using radiological or other conventional means; using said patient-specific anatomical data to determine the true, three-dimensional mechanical axis of said limb portion; providing a customized medical device capable of guiding a cutting tool in a plane transverse to said true, three-dimensional mechanical axis of a patient; providing a standard or customized prosthetic device; and, implanting said prosthetic device.

Further areas of applicability and other embodiments will become apparent from the detailed description provided hereinafter. It should be understood that the detailed description and specific examples, while indicating certain embodiment, are intended for purposes of illustration only and are not intended to limit the scope.

For these and for other purposes, it may be beneficial to provide a method of determining the true, three-dimensional mechanical axis of a patient's limb using patient-specific anatomical information.

Further, it may be beneficial to provide a cost-efficient method of determining the true mechanical axis of a patient's limb using non-invasive means.

Yet another benefit may be to provide a method of providing a customized surgical device capable of guiding a cutting tool in a plane transverse to said true, three-dimensional mechanical axis of a patient.

Additionally, it may be beneficial to provide an improved method of implanting a prosthetic device for a limb requiring little guesswork by a surgeon and yielding optimal performance for a particular individual.

Further features, aspects, and advantages of the present invention, as well as the structure and operation of various embodiments of the present invention, are described in detail below with reference to the accompanying drawings.

BRIEF DESCRIPTION OF THE DRAWINGS

The accompanying drawings, which are incorporated in and form a part of the specification, illustrate embodiments of the present invention and together with the description, serve to explain the principles of the invention. In the drawings:

FIG. 6a is a medial view of a distal femur illustrating one example of at least a first anatomical landmark;

FIG. 6b is a lateral view of a distal femur illustrating one example of at least a second anatomical landmark;

FIG. 7a is a medial view of a distal femur illustrating a first spatial relationship between a first and second anatomical landmark;

FIG. 7b is a lateral view of the first spatial relationship in FIG. 7a;

FIG. 8a is a distal end view of a femur further showing at least a third anatomical landmark defining a second spatial relationship;

FIG. 8b is an anterior view of FIG. 8a;

FIG. 8c is a medial view of FIG. 8a;

FIG. 9a is an anterior view of a distal femur further showing at least a fourth anatomical landmark;

FIG. 9b is a medial view of FIG. 9a;

FIG. 10b is a medial view of FIG. 10a;

FIG. 18b is an isometric proximal end view of FIG. 18a;

FIG. 19b is another view of FIG. 19a;

DETAILED DESCRIPTION OF THE EMBODIMENTS

Figures 1A, 1B:
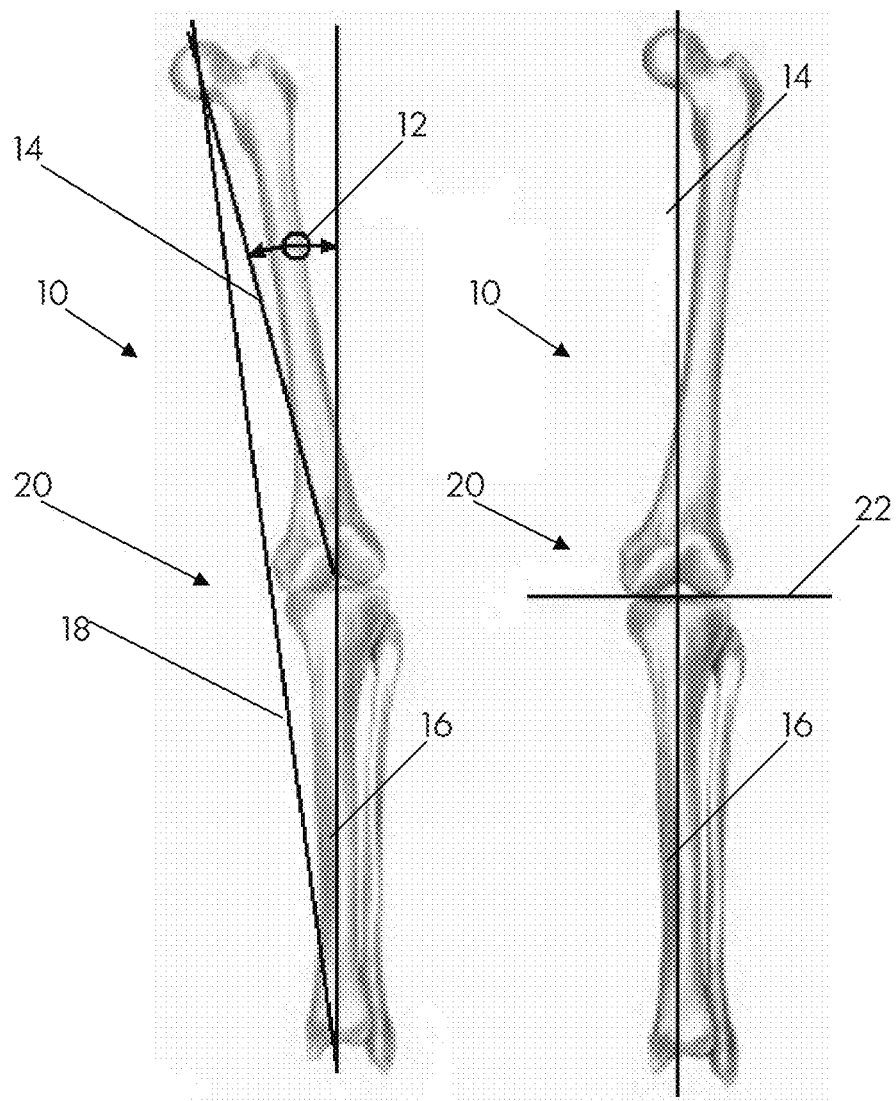
FIG. 1a is an anterior frontal view of a deficient lower limb.
FIG. 1b is an anterior frontal view of a normal lower limb.

Stresses within the knee joint are generally uniform and well balanced when the mechanical axis passes through the center of the knee joint. However, in many knee joint diseases, the mechanical axis is disturbed and does not pass through the center of the joint. Such a disturbance overloads portions of the knee joint, eventually leading to damage of even healthy tissue and cartilage. For example, if one condyle experiences degradation, the patella may not track symmetrically within the patellar groove on the femur. This may adversely affect Q-angle and cause anterior knee pain. A patient may compensate for a mal-aligned mechanical axis by modifying or adjusting their gait pattern to reduce knee pain. However, doing so may lead to other long-term problems such as hip, ankle, or back pain.

Thus, it is typically the task of a surgeon to restore the mechanical axis of the knee joint during a total or partial replacement surgery, such that that the mechanical axis will be restored and pass through the center of the new knee joint. This is commonly referred to "realigning" of the knee joint. In a correctly realigned position, the patella glides smoothly and symmetrically in its femoral groove, soft tissues are balanced and work equally, each condylar bearing surface is loaded equally, and a patient may return to a healthy and active lifestyle with reduced pain.

However, the performance of knee prosthetics may be greatly reduced if they are installed incorrectly. Aside from greater wear, an un-natural feeling, and a potential for knee pain, incorrect installation of knee prosthetics may have severe and even catastrophic consequences. For example, when a femoral component of a knee prosthesis is installed such that it is not properly aligned with the true mechanical axis of a patient, excessive shear forces may be present at the interface between bony surfaces and said prosthesis. The shear forces may weaken the cement bond over time, cause loosening or shifting of the prosthetic, fatigue the microstructure of implant components, adversely change kinematics and biomechanics of the joint, increase tension on soft tissue components, increase shear loads on other knee components such as the patella, and/or reduce the overall performance of the joint. In general, a total or partial knee prosthesis which is badly aligned with the mechanical axis will be overloaded, have potential for dislocation of the patella (or its prosthetic component), and will eventually need to be revised.

The methods surgeons currently use to determine mechanical axis are generally approximations. A drop rod may be used to roughly determine the mechanical axis, or a visual approximation may be made from a partial knee X-ray in a coronal plane. A surgeon may approximate the mechanical axis by feeling for the femoral head and looking at the ankle with respect to the knee joint. If a full leg x-ray is used, a surgeon may only estimate the mechanical axis in a single plane (i.e., two dimensions). While computer-assisted surgical (CAS) methods are accurate in helping to determine the mechanical axis of a patient's limb; many surgeons do not use these methods because they are expensive, require advanced skill, and generally add OR time.

The following description of the preferred embodiment(s) is merely exemplary in nature and is in no way intended to limit the invention, its application, or uses.

The method provides, in part, a method for providing a customized surgical device. The customized surgical device may generally be designed and created using patient-specific anatomical information. The customized surgical device may be, for instance, a cutting guide instrument utilized in a total or partial joint replacement surgical procedure. Said cutting guide instrument may be re-usable; however, for economical purposes, it is preferably disposable and made from an inexpensive plastics or other suitable biocompatible material. Since non-invasive pre-operative means (e.g., computerized tomography) are taken to appropriately size and analyze a patient's anatomy prior to surgery, redundant trialling steps during the surgical procedure, may be eliminated. Further advantages include reduced exposure and risk of infection. Moreover, pre-operative planning would allow a pre-sized standard or custom implant to be packaged with said cutting guide instrument.

It is preferred that the customized surgical device be configured to facilitate at least one bony resection perpendicular to the true, three-dimensional mechanical axis of a patient's limb.

While the customized surgical device is particularly well-suited for use in total knee arthroplasty (TKA), the usefulness is not limited to only lower limbs and/or extremities thereof. Rather, the present method may be equally suited for use with upper limbs and extremities (e.g., elbows, shoulders, wrists, and fingers).

FIG. 1a illustrates a lower limb (10) having a misaligned mechanical axis (18). The femoral mechanical axis (14) joins the tibial mechanical axis (16) at a displacement angle (12). Since the mechanical axis (18) of the lower limb does not pass through the centre of the knee joint (20), large stresses will be present in soft tissues as well as the bearing surfaces of the joint (20). In particular, excessive side shear stresses may be placed on joint components in the configuration shown in FIG. 1a.

FIG. 1b illustrates a lower limb (10) having a properly aligned mechanical axis. The femoral mechanical axis (14) joins the tibial mechanical axis (16) with little or no displacement angle. Since the mechanical axis of the lower limb (10) passes through the centre of the knee joint (20), stresses on soft tissues and bearing surfaces within the joint (20) will be uniform and balanced.

Figure 2:
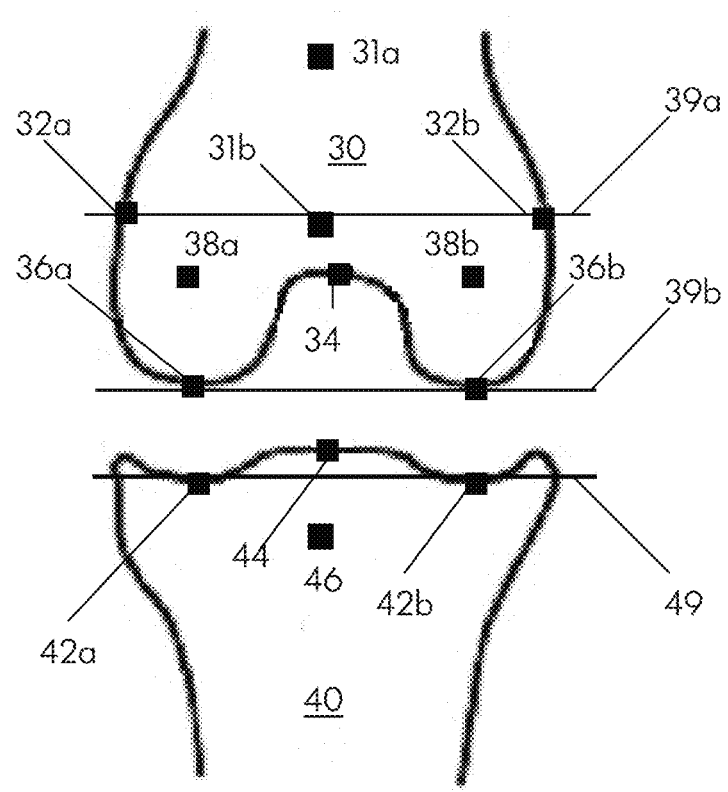
FIG. 2 is an anterior frontal view of a knee joint illustrating some examples of anatomical landmarks in a coronal plane.

FIG. 2 illustrates an anterior frontal view of a knee joint illustrating some examples of anatomical landmarks in a coronal plane. The knee joint comprises a femur (30) and a tibia (40). The femur (30) comprises many different anatomical landmarks including, but not limited to: upper anterior portion (31a), lower anterior portion (31b), lateral epicondyle (32a), medial epicondyle (32b), transepicondylar axis (39a), sulcus point (34), distal lateral condyle (36a), distal medial condyle (36b), lateral condyle center of mass (38a), medial condyle center of mass (38b), and distal medial-lateral condyle axis (39b). The tibia (40) comprises many different anatomical landmarks including, but not limited to: tibial tuberosity (46), lateral sulcus point (42a), medial sulcus point (42b), and apex of intercondylar eminence (44).

Figure 3:
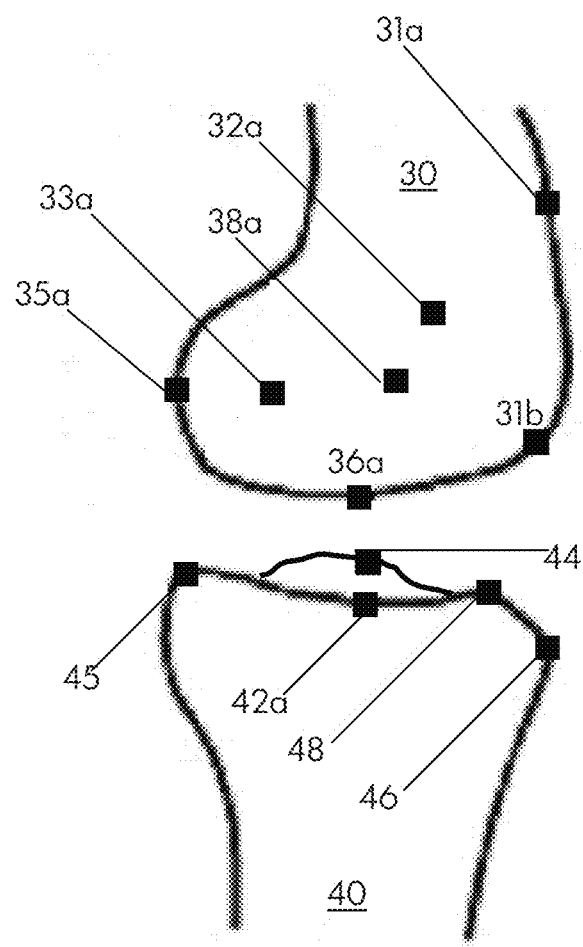
FIG. 3 is a lateral side view of a knee joint illustrating some examples of anatomical landmarks in a sagittal plane.

FIG. 3 illustrates a lateral side view of a knee joint illustrating some examples of anatomical landmarks in a sagittal plane. Shown on the femur (30) are many different anatomical landmarks including, but not limited to: upper anterior portion (31a), lower anterior portion (31b), lateral epicondyle (32a), distal lateral condyle (36a), lateral condyle center of mass (38a), posterolateral arc center (33a), and posterior lateral condyle (35a). Shown on the tibia (40) are many different anatomical landmarks including, but not limited to: tibial tuberosity (46), anterior tibial plateau (48), lateral sulcus point (42a), posterior tibial plateau (45), and apex of intercondylar eminence (44).

Figure 4:
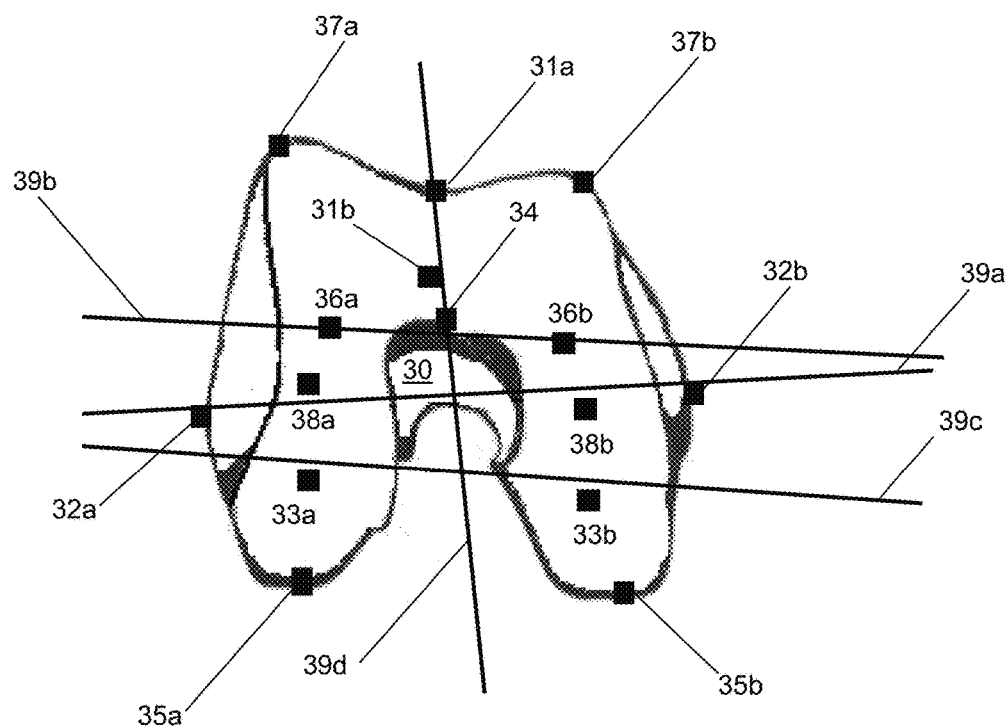
FIG. 4 is a distal end view of a femur illustrating some examples of anatomical landmarks in a transverse plane.

FIG. 4 illustrates a distal end view of a femur illustrating some examples of anatomical landmarks in a transverse plane. Shown on the femur (30) are many different anatomical landmarks including, but not limited to: upper anterior portion (31a), lower anterior portion (31b), Whitesides line (39d), lateral epicondyle (32a), medial epicondyle (32b), transepicondylar axis (39a), sulcus point (34), distal lateral condyle (36a), distal medial condyle (36b), distal condylar axis (39b), lateral condyle center of mass (38a), medial condyle center of mass (38b), posterolateral arc center (33a), posteromedial arc center (33b), posterior arc center axis (39c), posterolateral condyle (35a), posteromedial condyle (35b), and distal medial-lateral condyle axis (39b).

Figure 5:
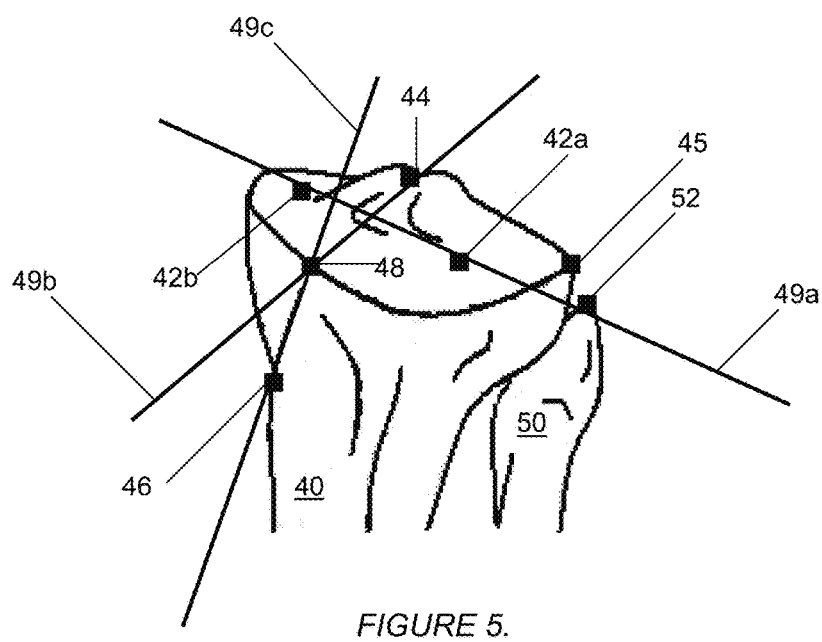
FIG. 5 is a proximal end perspective view of a tibia illustrating some examples of anatomical landmarks in a transverse plane.

FIG. 5 illustrates a proximal end perspective view of a tibia and fibula, illustrating some examples of anatomical landmarks in a transverse plane. Shown on the tibia (40) are many different anatomical landmarks including, but not limited to: tibial tuberosity (46), anterior tibial plateau (48), apex of intercondylar eminence (44), tibial A-P axis (49b), lateral sulcus point (42a), medial sulcus point (42b), posterolateral tibial plateau (45), tibial M-L axis (49a), and axis (49c) connecting the tibial tuberosity (46) with the anterior tibial plateau (48). Shown on the fibula (50) is the fibular head crest (52).

It is to be understood that the anatomical landmarks shown in FIGS. 2-5 and discussed herein are exemplary in nature and should in no way limit the definition of anatomical landmark. Rather, the term anatomical landmark is herein defined as a readily identifiable feature within or on a limb. The limb, may be, for instance, an arm or a leg. For example, an anatomical landmark may comprise a prominent portion of an ulna or humerus (e.g., centroid of the humeral head). In other instances, an anatomical landmark may comprise the centroid of a femoral head or superiormost apex of the talus bone between the medial and lateral malleolus.

Figure 12:
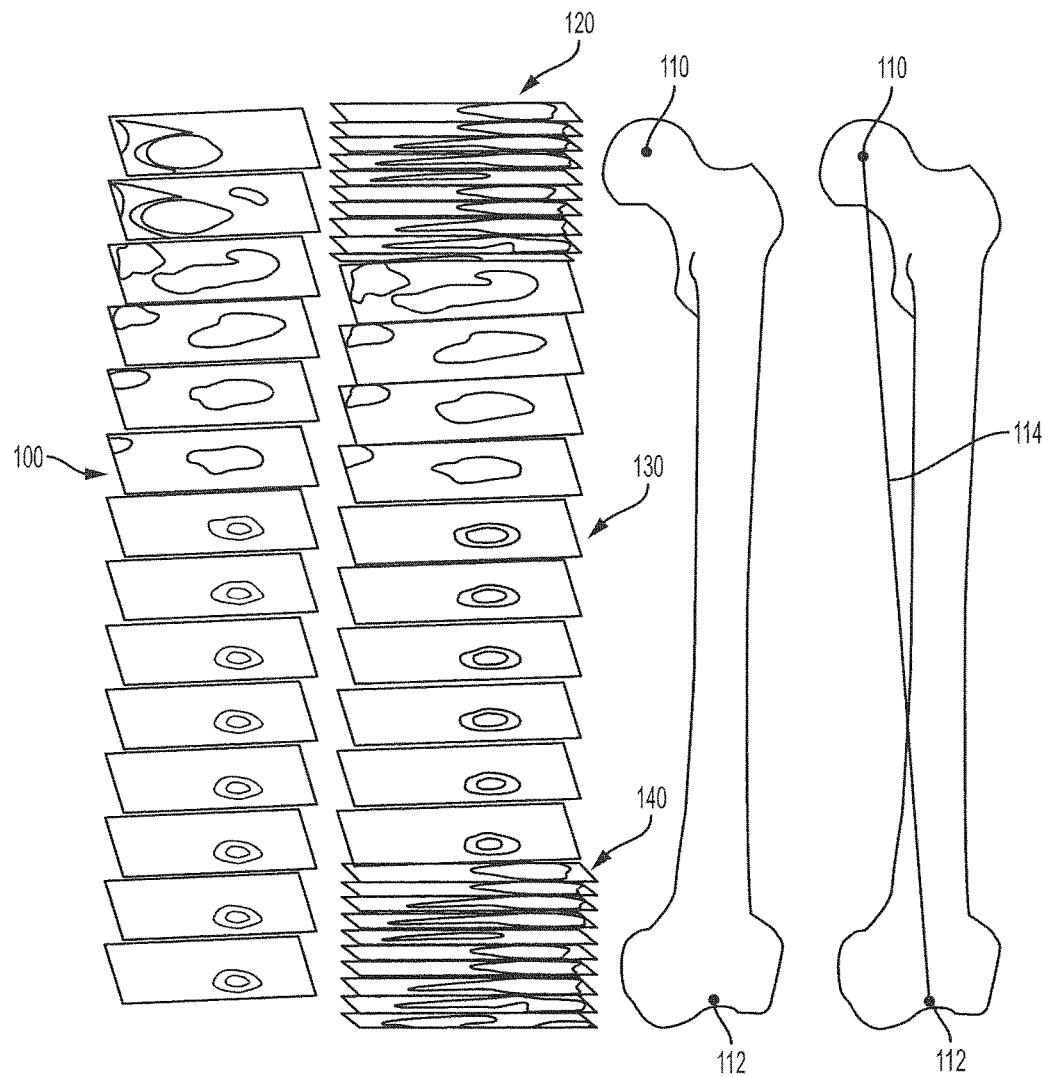
FIG. 12 illustrates a first method of determining a mechanical axis using non-invasive means.

In other favourable embodiments, anatomical information corresponding to a patient's limb is gathered pre-operatively using non-invasive means (100). Such means, as shown in FIG. 12 may comprise, for instance, radiological imaging, computerized tomography, MRI scans, CT/CAT scans, X-ray, contrast MRI's, ultrasonic means, and/or other conventional means. The patient-specific anatomical information gathered by said means may be pre-processed and converted to form a three-dimensional CAD model, or it may be used in its raw form to identify key anatomical landmarks (110,112) of interest within a patient's limb. In preferred embodiments, the anatomical data (100) is used to determine the true, three-dimensional mechanical axis (114) of a particular patient's limb prior to designing the customized surgical device for said patient. First, a proximal portion (110) of a patient's limb identified. In the case of determining the true, three-dimensional mechanical axis of a patient's leg, the proximal portion (110) may be, for example, a centroid of the femoral head as shown in FIG. 12. Secondly, a more distal portion (112) of a patient's limb is determined. For example, said more distal portion (112) may be the superiormost apex of a talus bone, measured ankle centre, or some point lying on an axis connecting the medial and lateral malleolus. Alternatively, said more distal portion (112) may be a sulcus of the intercondylar/trochlear groove as shown in FIG. 12. It is to be noted that each of said proximal (110) and distal (112) portions have a defined spatial coordinate in three dimensions, and that the sequence in which each portion (110,112) is identified is not particularly important. Thirdly, the true, three-dimensional mechanical axis (114) of a patient is determined by projecting and extending an imaginary line between said proximal portion (110) and said distal portion (112) of a patient's limb in a shared coordinate system. Lastly, a customized surgical device is provided, said customized surgical device being advantageously configured to guide a cutting tool perpendicular in some way to said true, three-dimensional mechanical axis (114). For simplicity, design of the customized surgical device may be performed in a new coordinate system which uses said true, three-dimensional mechanical axis (114) as one of its three axes (e.g., Y-axis).

Alternatively, as shown in FIG. 12, a full limb scan may be taken, wherein the axial resolution of the full limb scan between the proximal (110) and distal (112) portions is higher in areas (120,140) adjacent to the proximal (110) and distal (112) portions, respectively, than at limb portions (130) further away from the proximal (110) and distal (112) points of interest. The change in resolution of the scan along the limb axis may be instantaneous, gradual, or a step function. In doing so, the fewer number of central scans (130) provide an energy efficient means to more accurately locate proximal (110) and distal (112) portions relative to each other, as well as obtain some information about the anatomical axis, without prolonging a patient's radiation exposure and undue stress.

Figure 13:
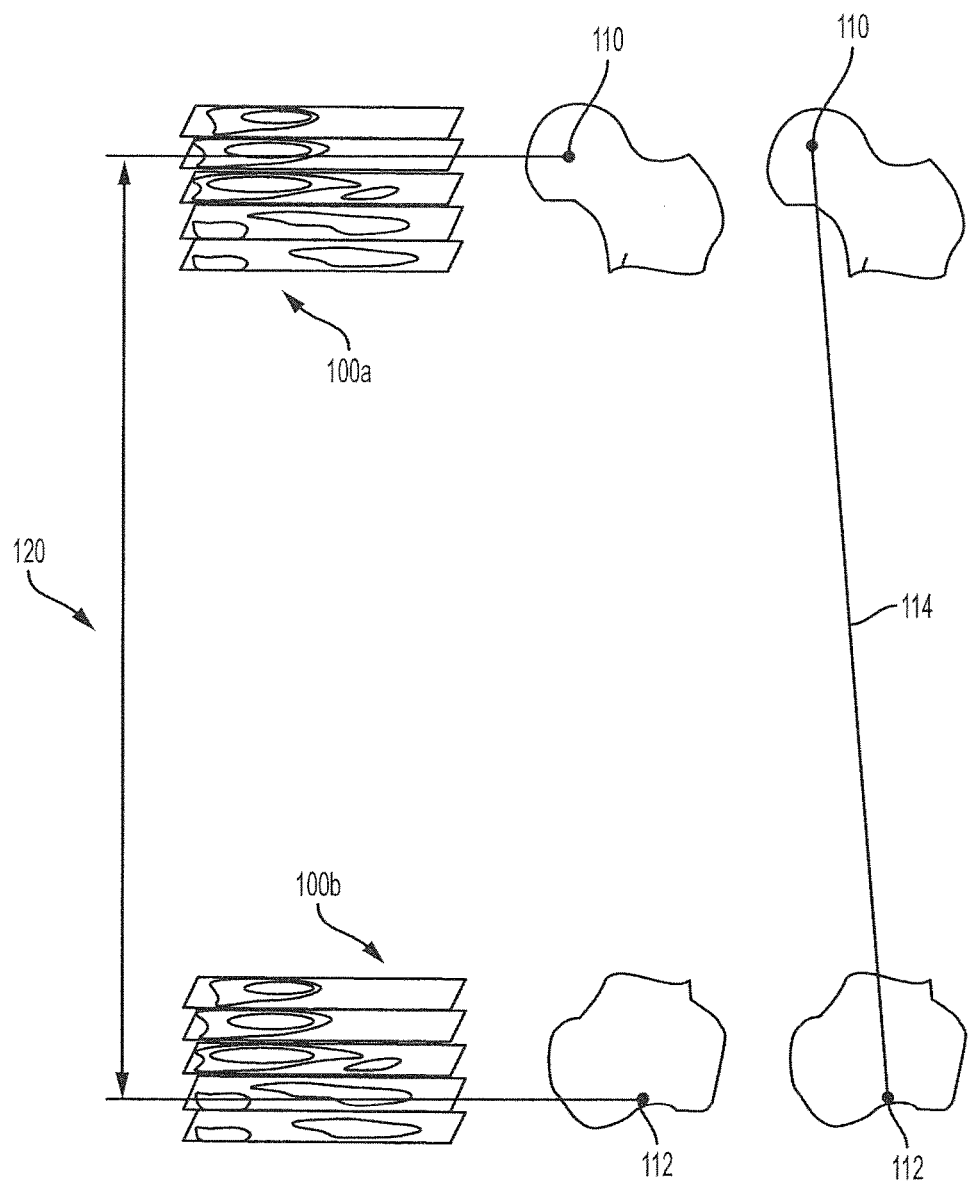
FIG. 13 illustrates a second method of determining a mechanical axis using non-invasive means.

As illustrated in FIG. 13, for economical purposes, one or more partial scans (100a,100b) of a patient's limb may be utilized in lieu of the full limb scan (100) shown in FIG. 12. When using such partial scans (100a,100b) of a patient's limb, the exact location of each scan relative to the patient's limb may be carefully noted to ensure that the scans (100a, 100b) are spaced apart in all directions correctly before extrapolating the mechanical axis (114). In much the same method as discussed above, a proximal portion (110) and a distal portion (112) of a limb is determined Each of the proximal (110) and distal (112) portions have their own, three-dimensional spatial coordinate, and are spaced in relationship on a given coordinate system according to CT data. It may, for instance, be necessary to know the exact distance (120) between said one or more partial scans (100a, 100b) to accurately determine the true, three-dimensional mechanical axis (114) of the limb. Preferably, the partial scans (100a,100b) are performed sequentially or simultaneously on the same machine and in a shared coordinate system, so that the step of determining the relative spatial locations of the proximal (110) and distal (112) portions and their associated scans (100a,100b) can be readily achieved without difficulty. A third and fourth partial scan (not shown) may be taken intermittently at predetermined points between the proximal (110) and distal (112) portions to identify deformities and/or determine a more accurate location of the true, three-dimensional mechanical axis in space as well as the anatomical axis.

Figure 14:
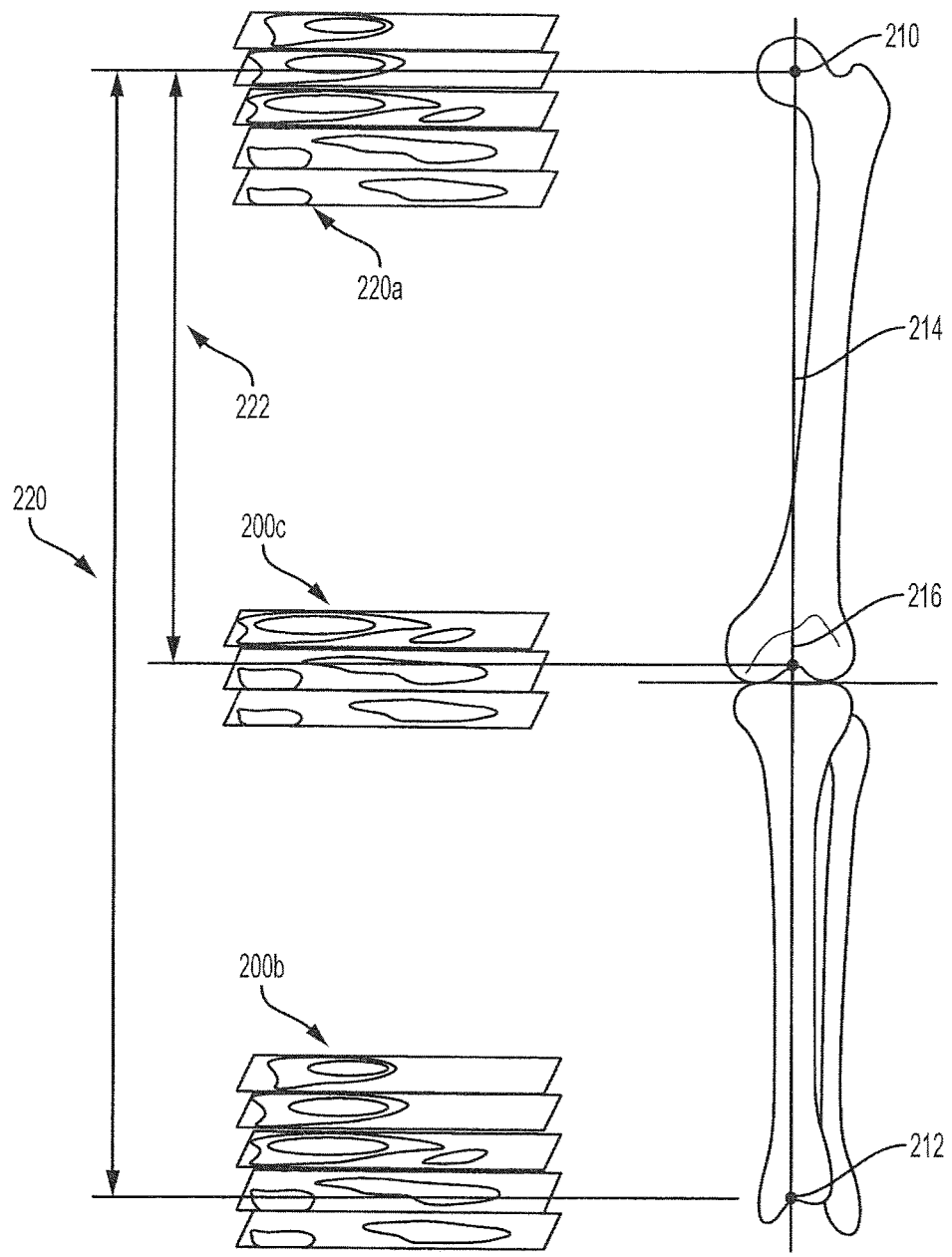
FIG. 14 illustrates a third method of determining a mechanical axis using non-invasive means.

For instance, as shown in FIG. 14, a central partial scan (200c) may be taken at a central portion (216) of a limb as well as proximal (210) and distal (212) portions. In some embodiments, the proximal portion (210) may be the centroid of a femoral head, and the distal (212) portion may be a central malleolus portion on the distal tibia adjacent the talus. After determining the distances (220) and/or relative spatial location between the proximal (200a) and distal (200b) scans, the true, three-dimensional mechanical axis of a limb (214) may be determined in space by projecting an imaginary line between the proximal (210) and distal (212) portions. The partial scan (200c) taken at a central portion (216) of the limb may be used to slightly adjust the mechanical axis (214) in space prior to providing the customized surgical device, and/or serve as a reference point to see what adjustments need to be built into the customized surgical device. The central portion (216) may also be used to check whether or not the mechanical axis (214) intersects the centre of the joint.

One problem found in the prior art which may affect the above methods is that a patient might move during radiological imaging. This problem is especially common in CT and MRI scans, since the duration of an MRI or CT scan can extend to upwards of 45 minutes or more. If any motion by the patient occurs during imaging, artifacts may appear in the scan, which could render the scan unusable. Moreover, the relative positions of anatomical landmarks may be compromised if a patient moves during a scan. This problem increases costs for healthcare organizations, and/or may result in inaccurate diagnosis for a patient.

Therefore, according to some embodiments, it may be desirable to stabilize or orientate a patient's limb prior to or during the step of obtaining digital images of a patient's anatomy. In some instances, it may be also be desirable to determine the exact position and/or orientation of a joint (e.g., knee joint) relative to the rest of the limb in order to accurately determine where to place bony resections such that they are perpendicular to the true, three-dimensional mechanical axis of a patient's limb. In doing so, the ideal placement of an implant is determined such that desired in vivo loading conditions are achieved. Stabilization may be accomplished in any one or more of the methods discussed below.

In some instances, a jig may be used to stabilize a patient's limb while undergoing radiological, magnetic resonance, or computerized tomographical (CT) imaging. A "table template" comprised of lines, ridges, or other features located on a scanning table may be used alone or with other methods to maintain a patient's limb in a particular orientation during a scan. The imaging equipment may be aligned and oriented with said table template such that any angulation in the MR image is due to the patient deviation from nominal.

Some embodiments may incorporate at least one jig comprising a leg brace or external fixation frame. The jig may be universally adapted for use with hip, pelvis, knee, foot, or ankle joints as well as shoulder, elbow, wrist, and hand joints—or the jig may be specific for a particular portion of an affected limb. The jig may be adapted to maintain a patient's limb in multiple relaxed states of extension and flexion, or may force a patient's limb into a corrective or other alignments and orientations. The jig essentially ensures that no movement will occur during the scan. However, while the main purpose of the jig is to stabilize the limb, it may also advantageously serve as a means to convey important patient-specific limb information (e.g., true, three-dimensional mechanical axis) if the required limb info cannot be directly imaged.

Another problem with conventional 3D imaging is a blending of bones between joints having thin or deteriorated cartilage. In some instances, radiograph-translucent cartilage between joint bones is worn, and so articulating surfaces appear as one in radiographs with no space therebetween. Therefore, a jig according to some embodiments may employ means for joint distraction including clamps, vises, worm threads, pistons, etc. to separate joint bones by a predetermined amount prior to imaging. By distracting the joint bones, articulating surfaces will image uniquely and indications will be clearer and more accurate. Moreover, a better determination of the true, three-dimensional mechanical axis of a patient's limb may be made.

Percutaneous intervention should not be required; however, a jig according to some embodiments may comprise percutaneous means for grasping and orienting portions of a patient's limb, and/or percutaneous means for distraction. Less-invasive external contact means may alternatively, and more preferably be employed, said less-invasive external contact means including soft touch points which may be placed against the outer skin, muscle, bone, ligaments, and/or soft tissue. Gentle pressure may be subsequently applied at said soft touch points to rigidly brace and lock down multiple degrees of freedom of the limb prior to and/or during a digital scan. Radiograph-transparent or translucent padding may advantageously be employed. The materials of the jig or brace will generally be such that they do not interfere with the imaging, and are similar in nature to the bed materials. Plastics materials are generally preferred, although other suitable materials are expected.

Small markers may be incorporated into the jig and the jig provided in such a manner so as to indicate the true, three-dimensional mechanical axis of the patient thru said image markers. Such markers may be placed on or within the jig including but not limited to portions of said percutaneous pins, said external contact means, or other attachment devices such as bands placed around the patient's limb. Alternatively, the markers may be superimposed in space by triangulating from one or more reference markers at known locations of the jig. For example, a jig may be adjusted to a patient in such a way that the spatial location of the patient's hip centre is readily determined in space. A technician performing a digital scan according to methods may utilize a laser line, outrigger assembly, or visual assessment to properly align the jig to the hip, knee centre, and ankle centre. When imaged, these markers can be configured so as to define one or more true, three-dimensional patient-specific limb axes. Said one or more patient-specific limb axes may be defined as any one or more of the following without limitation: femoral mechanical axis, tibial mechanical axis, leg mechanical axis, arm mechanical axis, humeral mechanical axis, and/or ulna mechanical axis.

Construction of jigs according to some embodiments could be made from a homogeneous quick mold of the patient's limb (e.g., temperature forms, impression molds, conventional casting materials, or other methods). Alternatively, construction of jigs according to other embodiments may include constructs comprising one or more pieces. Components of a jig may comprise numerous variations in materials, which may be selectable according to the amount of stability needed or the orientation desired. Different levels of hardness may be used to selectively optimize patient comfort while still achieving an ideal orientation of said patient's limb.

In preferred embodiments, it is desirable to place at least one bony resection of a limb perpendicular to its true, three-dimensional mechanical axis, in order to avoid excessive side shear forces on an implant. In other words, it is desirable to position an implant such that at least one bone-interfacing portion of the implant is perpendicular to the true, three-dimensional mechanical axis, because this ensures that all or most of the load applied to a patient's limb travels through the implant evenly and uniformly, thereby avoiding transverse shear which could cause cement cracking and eventual loosening of the implant. Loosening of the implant may lead to increased pain, reduced performance, soft tissue impingement, and may ultimately lead to catastrophic failure and invasive revision procedures.

However, it may not always be economically possible to determine the true, three-dimensional mechanical axis using the abovementioned non-invasive means (100,100a,100b, 100c,120,130,140). Instead, it may be necessary to use alternative methods of approximating the true, three-dimensional mechanical axis of a patient using only a single, partial scan, said methods being improvements over the prior art methods previously mentioned. FIGS. 6a-11 illustrate such embodiments. FIGS. 6a-11 show some of the various steps utilized in providing a customized surgical device according to some embodiments. Particularly, FIGS. 6a-11 illustrate embodiments for use in total knee arthroplasty where a full leg scan is not possible or practical.

FIGS. 6a and 6b illustrate a first step of providing a customized surgical device, said first step comprising identifying at least a first and second anatomical landmark. As shown in FIG. 6a, a first anatomical landmark (32b) may be selected by identifying a prominent portion of the medial epicondyle of a distal femur (30). As shown in FIG. 6b, a second anatomical landmark (32a) may be selected by identifying a prominent portion of the lateral epicondyle of a distal femur (30).

FIGS. 7a and 7b illustrate a second step of providing a customized surgical device, said second step comprising establishing a first special relationship (39a) from the at least first (32b) and second (32a) anatomical landmarks. Particularly, FIGS. 7a and 7b illustrate a first special relationship (39a) comprising a line connecting first (32b) and second (32a) anatomical landmarks. The line shown (39a) may be, for instance, the transepicondylar axis of a femur (30) or any other spatial relationship such as a point, line, or plane.

FIGS. 8a-8c illustrate a third step of providing a customized surgical device, said third step comprising identifying at least a third anatomical landmark (34), to establish a second special relationship (34a). Particularly, FIGS. 8a-8c illustrate a second special relationship (34a) comprising a line which runs through the third anatomical landmark (34) and which is parallel with said first special relationship (39a). As shown in FIGS. 8a-8c, the third anatomical landmark (34) may be, for example, a sulcus portion of the intercondylar/trochlear groove of a femur (30).

Turning now, to FIGS. 9a and 9b, there is illustrated a fourth step of providing a customized surgical device, said fourth step comprising identifying at least a fourth anatomical landmark (31a) on a patient's limb. The fourth anatomical landmark (31a) as shown in FIGS. 9a and 9b may be, for example, the anteriormost portion of a distal femur (30) which may not cause notching of the femur when making a planar anterior resection for a femoral component of a knee prosthesis (e.g., anterior cortex).

Figure 10B:
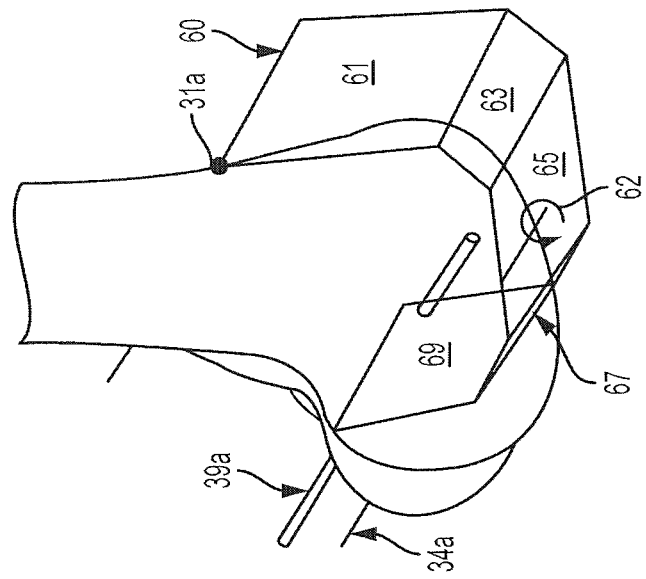
Figure 10A:
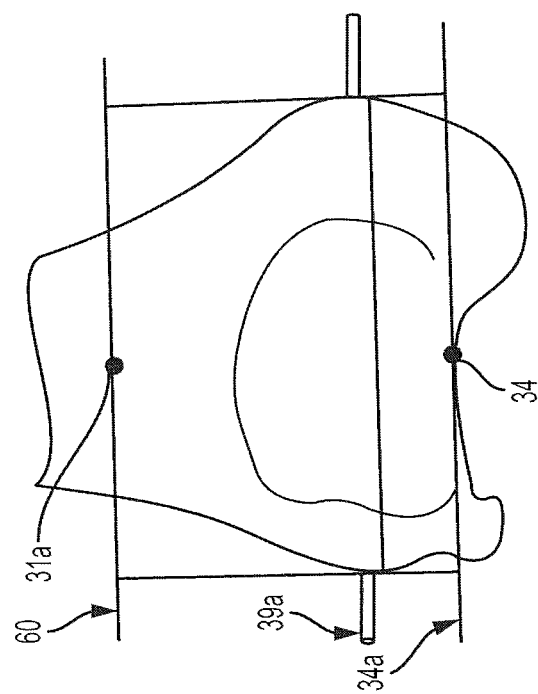
FIG. 10a is an anterior view of a distal femur showing a superimposed profile thereon.

Referring to FIGS. 10a and 10b, there is illustrated a fifth step of providing a customized surgical device, said fifth step comprising positioning a profile (60) for said limb in all degrees-of-freedom but one degree-of freedom (62). In the instance of total knee arthroplasty, said profile (60) may be a box-cut profile for a distal femur (30). The box cut profile (60) may include, for instance, an anterior cut (61), anterior chamfer cut (63), distal cut (65), posterior chamfer cut (67), and posterior cut (69). The relative angles between each cut of the profile (60) may differ, and may be standard, generic, or custom for optimized bone conservation and or performance needs of a particular patient. Alternatively, the profile (60) may include rounded cuts so long as at least one portion of the profile (60) is parallel to the first spatial relationship (39a). The profile (60) is preferably fixed in the following degrees-of-freedom: varus/valgus, internal/external rotation, A/P, M/L, and Sup./Inf. The profile (60) is preferably allowed to move in at least one remaining degree-of-freedom (e.g., flexion angle rotation, 62). The profile (60) is then fixed in said last degree-of-freedom such that a portion of said profile (60) passes through the fourth anatomical landmark (31a). The distal cut portion (65) of the profile (60) may alternatively be shifted in a superior-inferior axis so as to remove or conserve as much bone as is necessary. It should be noted that the remaining degree-of-freedom may be one other than rotation in flexion/extension angle (62). Rather, the remaining degree-of-freedom may comprise any one of those abovementioned. Lastly, a customized surgical device is provided, said customized surgical device being configured to guide a cutting tool along at least a portion of the profile (60).

It is believed that by following the method steps provided in the algorithm discussed above, an implant is more likely to be positioned in line with the true, three-dimensional mechanical axis of a limb.

Figure 11:
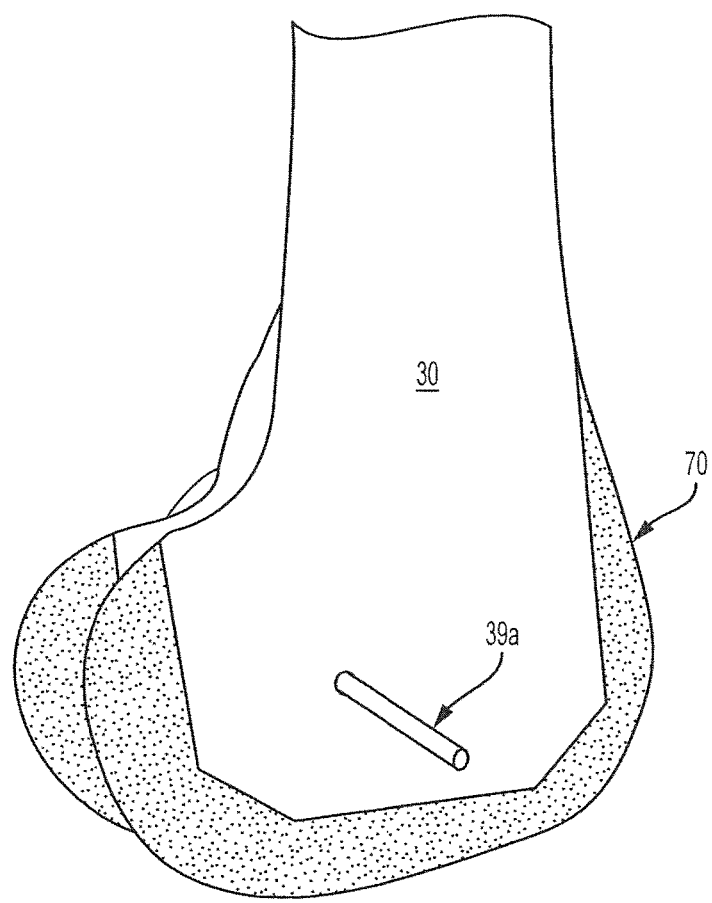
FIG. 11 is a medial view of a distal femur which has been resected along the superimposed profile in FIG. 10a and replaced with an implant.

As shown in FIG. 11, an implant is attached at the points of resection to restore natural kinematics, biomechanics, and kinetics to the joint. Shown in FIG. 11 is a femoral component (70) of a knee prosthesis attached to a resected distal femur (30). The interface between the femur (30) and the femoral component (70) generally shares the shape of said profile (60) shown in FIGS. 10a and 10b. The distal interface between the femur (30) and the femoral component (70) is related to the distal cut plane (65) of said profile (60) and is generally perpendicular to the true, three-dimensional mechanical axis. Therefore, the implant (70) is less susceptible to avoidable side shear loading.

In some embodiments, it may be necessary to iteratively change the positioning of resection planes to optimize performance, maximize bone conservation, and avoid impingement with soft tissue and/or properly fit a standard prosthesis to a patient that is "in-between" sizes. Such iterative manipulations may be done in a computer aided program with finite element anaylysis (PEA). Examples of useful programs are LifeMOD and KneeSIM by Orthopaedic Research Laboratories, Inc.

Figure 18A:
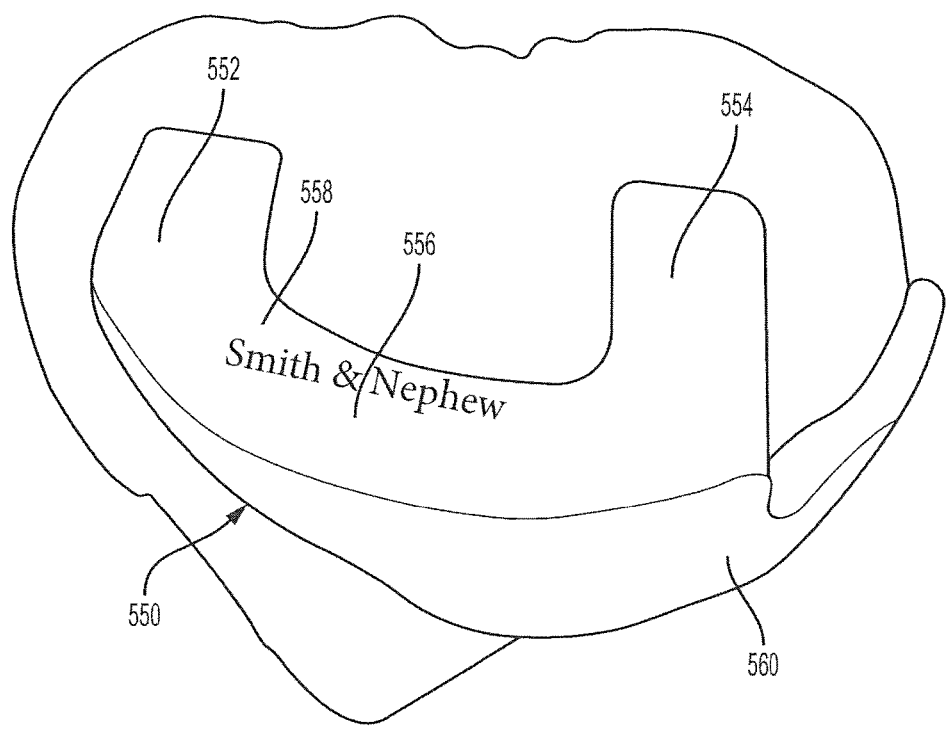
FIG. 18a is a proximal end view of a tibia having thereon a customized surgical device according to some embodiments.
Figure 18B:
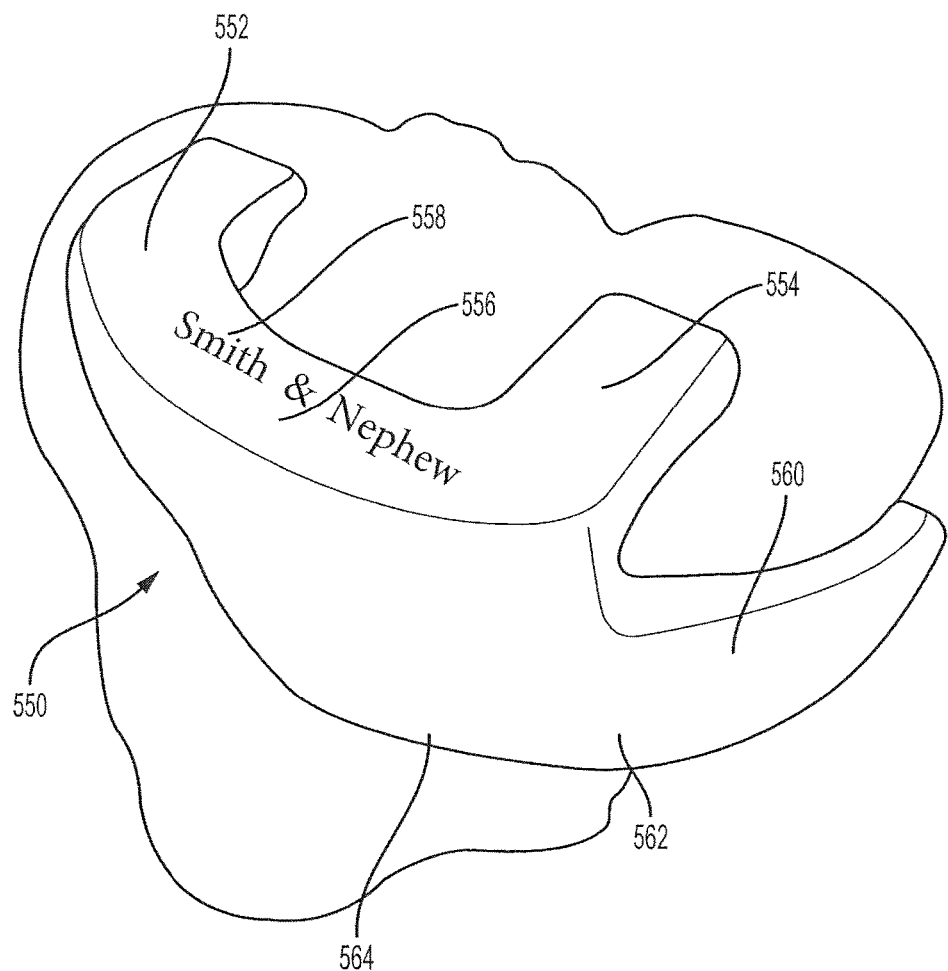

In some embodiments, as shown in FIGS. 18a and 18b, a customized surgical device (550) may facilitate a proximal tibial resection perpendicular to the true, three-dimensional mechanical axis of a lower limb. The customized surgical device (550) may comprise a cutting slot (560) or other equivalent means for guiding a cutting tool (e.g., oscillating surgical saw blade) perpendicular to the true, three-dimensional mechanical axis of a lower limb. In some instances, said customized surgical device (550) may utilize a single flat planar surface to guide said cutting tool. The cutting slot (560), if used, may be open or closed at one end and may or may not have side edges configured to control or limit resection (e.g., avoid cutting ACL/PCL attachment bone near intercondylar eminence). Shown in FIGS. 18a-b is one non-limiting example of a customized surgical device (550), which conforms at least in part to a bony surface of an individual's limb. The customized surgical device shown is adapted for facilitating at least a partial tibial resection on a medial side, said resection being perpendicular to the true, three-dimensional mechanical axis of a patient's lower limb. This type of orthogonal resection may be advantageously used in unicompartmental, bi-compartmental, or total knee replacement procedures to ensure that the forces acting on a tibial tray and/or insert are mainly concentrated in compression along the mechanical axis and not in side-to-side shear. While the shown customized surgical device is adapted for use in performing a full or partial tibial resection, other customized surgical devices may be configured for facilitating total or partial resections on other limb bones such as those in an upper limb or extremity (e.g., elbow or wrist).

Customized surgical devices may extend transversely across different portions of a bone along a portion of or along the entire width of the bone. Said devices may employ one or more cutting slots or planar surfaces to guide a cutting tool perpendicular to the true, three-dimensional mechanical axis of a limb in various ways as shown in FIGS. 21a-21i. The customized surgical device (550) may be made of a biocompatible metallic or plastics material, may be made disposable for convenience, and may further comprise indicia (558). Indicia (558) may comprise any one or more of the following without limitation: a logo, a trademark, device serial number, patient-specific data such as a name, DOB, patient number, or social security number, and/or other instructions indicating correct placement (e.g., "RIGHT-MEDIAL-TIBIA"). The customized surgical device (550) may be configured to facilitate medial, lateral, anterior, posterior, or total bony resections, and may comprise one or more means for temporary bone fixation (562,564) to prevent said customized surgical device (550) from shifting when in use and/or under vibration of a cutting tool. Such means (562,564) may be, for instance, holes for pins as shown. The holes may be in any position relative to each other (e.g., parallel, oblique, perpendicular, skewed, offset, etc.). In order to ensure a more accurate placement of the customized surgical device (550) onto a patient's natural bone, one or more body portions (552,554,556) may be present to form a larger surface contact area and stabilize the customized surgical device (550) in multiple directions in space. The body portions (552,554,556) may be configured to allow increased frictional contact between a bony surface and said customized surgical device (550) while avoiding excessive contact with soft tissue. It will be readily apparent to those of ordinary skill in the art that the exact shapes and sizes of body portions (552,554,556) may differ between patients, and may also for differ for bony resections in different limbs and portions thereof for best fit with a particular bony structure.

The customized surgical device (550) may be formed from a standard sized or shaped template block, which is then modified to comprise an inner bone-interface profile which is unique to an individual patient, and custom guide means such as a cutting slot or planar surface which is configured to guide a cutting tool perpendicular to the true, three-dimensional mechanical axis unique to said individual patient.

Figure 19A:
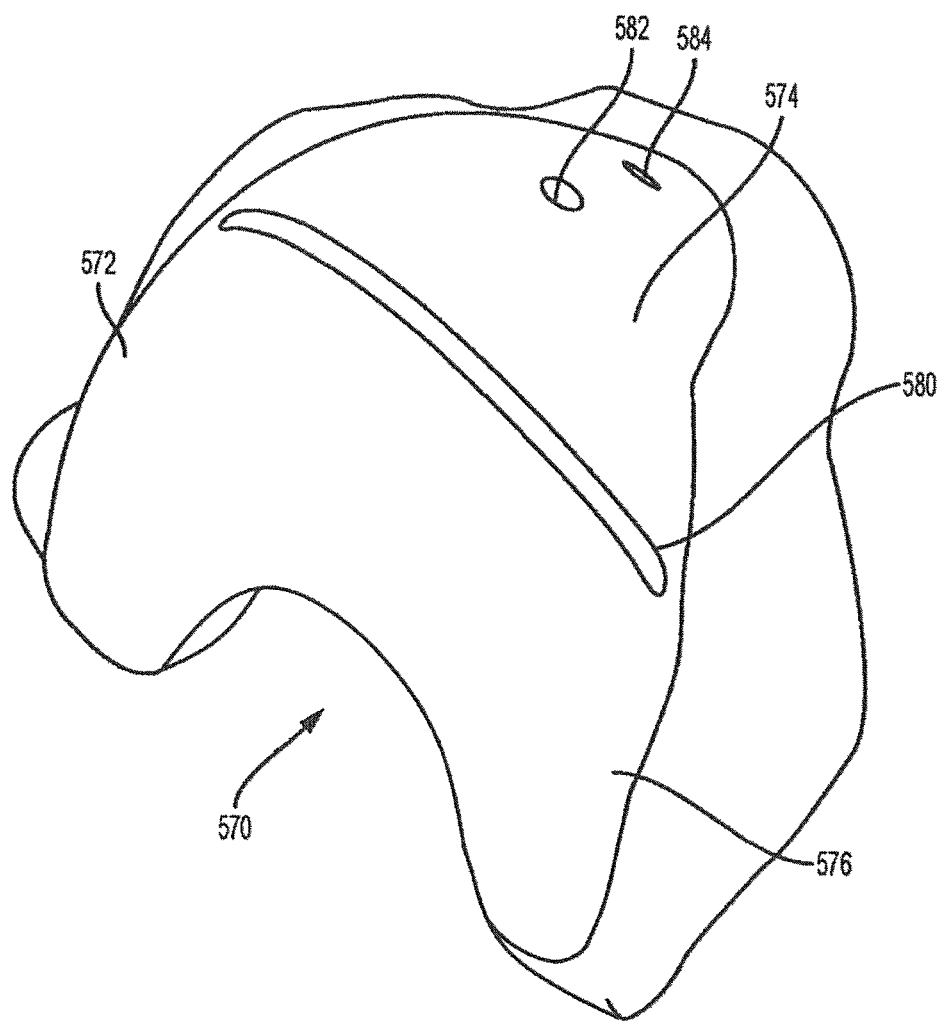
FIG. 19a is an isometric distal frontal view of a femur having thereon a customized surgical device according to other embodiments.
Figure 19B:
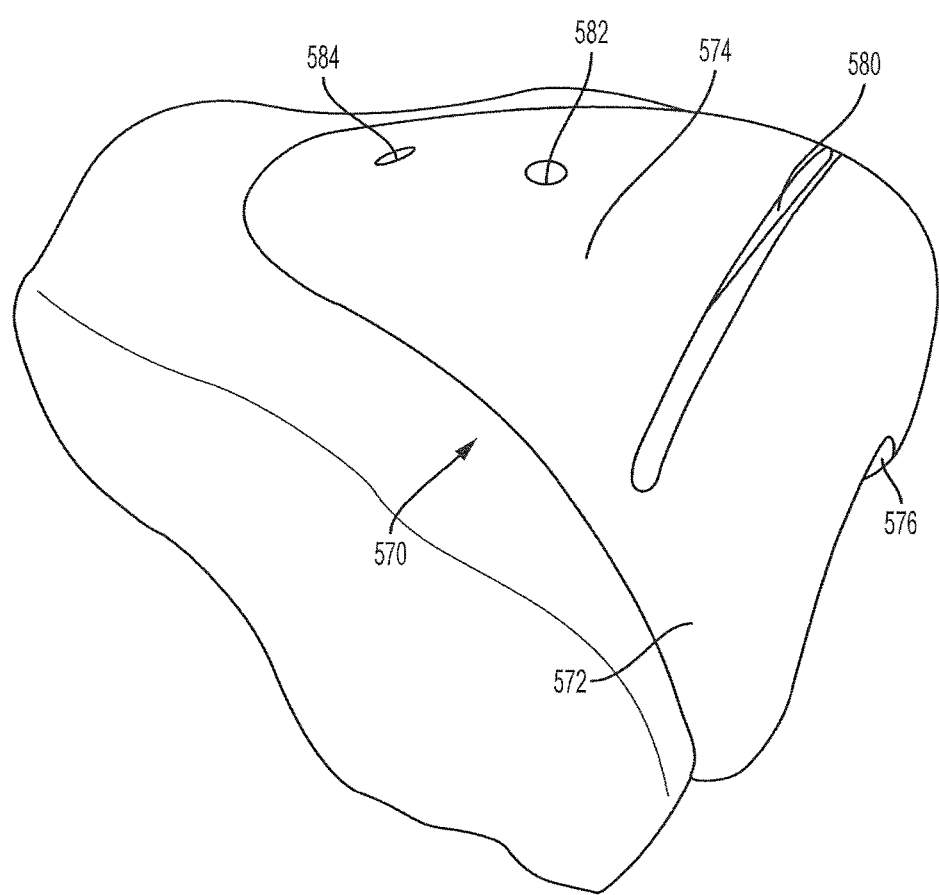

In other non-limiting embodiments, a customized surgical device may be provided for use with other portions of a lower limb. FIGS. 19a and 19b illustrate a customized surgical device (570) for use with a femur; said device (570) comprising a means (580) for guiding a cutting tool perpendicular to the true, three-dimensional mechanical axis of a leg. In the instance shown, the customized surgical device generally conforms at least in part to a bony surface of an individual's distal femur. The customized surgical device (570) is generally adapted for facilitating at least a partial femoral resection on a medial side, a partial femoral resection on a lateral side, or a full femoral resection across the entire width of the bone; said resection being perpendicular to the true, three-dimensional mechanical axis. A cutting slot or other equivalent means (580) for guiding a cutting tool perpendicular to the true, three-dimensional mechanical axis of a leg limb may be employed. In some instances, said customized surgical device (570) may utilize a flat planar surface to guide said cutting tool. The cutting slot, if used, may be open or closed at one end and may or may not have side edges configured to control or limit resection. The customized surgical device (570) may have one or more means for temporary bone fixation (582,584) to prevent said customized surgical device from shifting when in use and/or under vibration. Such means (582,584) may be, for instance, holes for pins as shown. The holes may be in any position relative to each other (e.g., parallel, oblique, perpendicular, skewed, offset, etc.). In order to provide a more accurate placement of the customized surgical device (570) onto a patient's natural bone, one or more body portions (572,574, 576) may be present to form a larger surface contact area and stabilize the customized surgical device (570) in multiple directions in space. The body portions (572,574,576) may be configured to allow maximum or optimal contact between a bony surface and said customized surgical device (570) while avoiding excessive contact with soft tissue. It will be readily apparent to those of ordinary skill in the art that the exact shapes and sizes of body portions (572,574,576) may differ between patients, and may also for differ for bony resections in different limbs and portions thereof for best fit with a particular bony structure.

Figure 20:
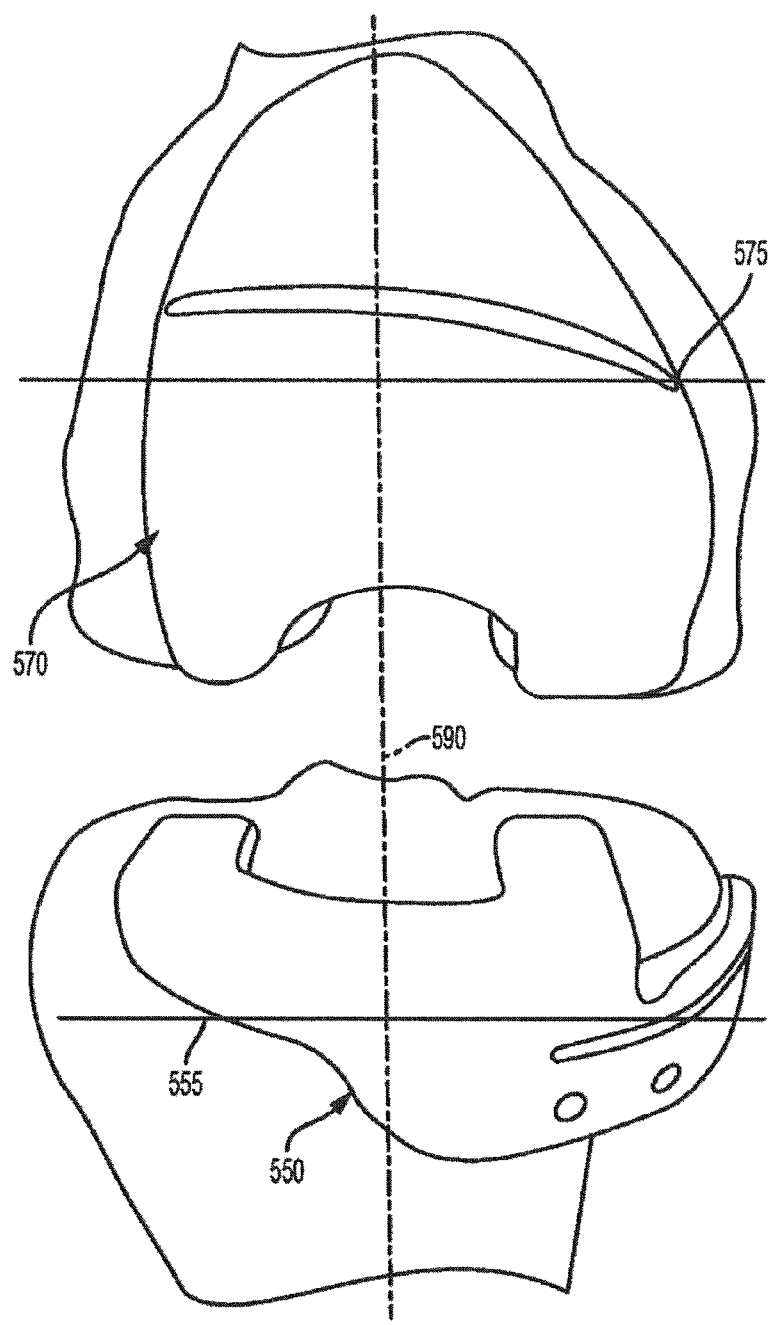
FIG. 20 is an anterior frontal view of a femur and tibia each having thereon, customized surgical devices according to some embodiments.
Figures 21A, 21B, 21C, 21D, 21E, 21F, 21G, 21H, 21I:
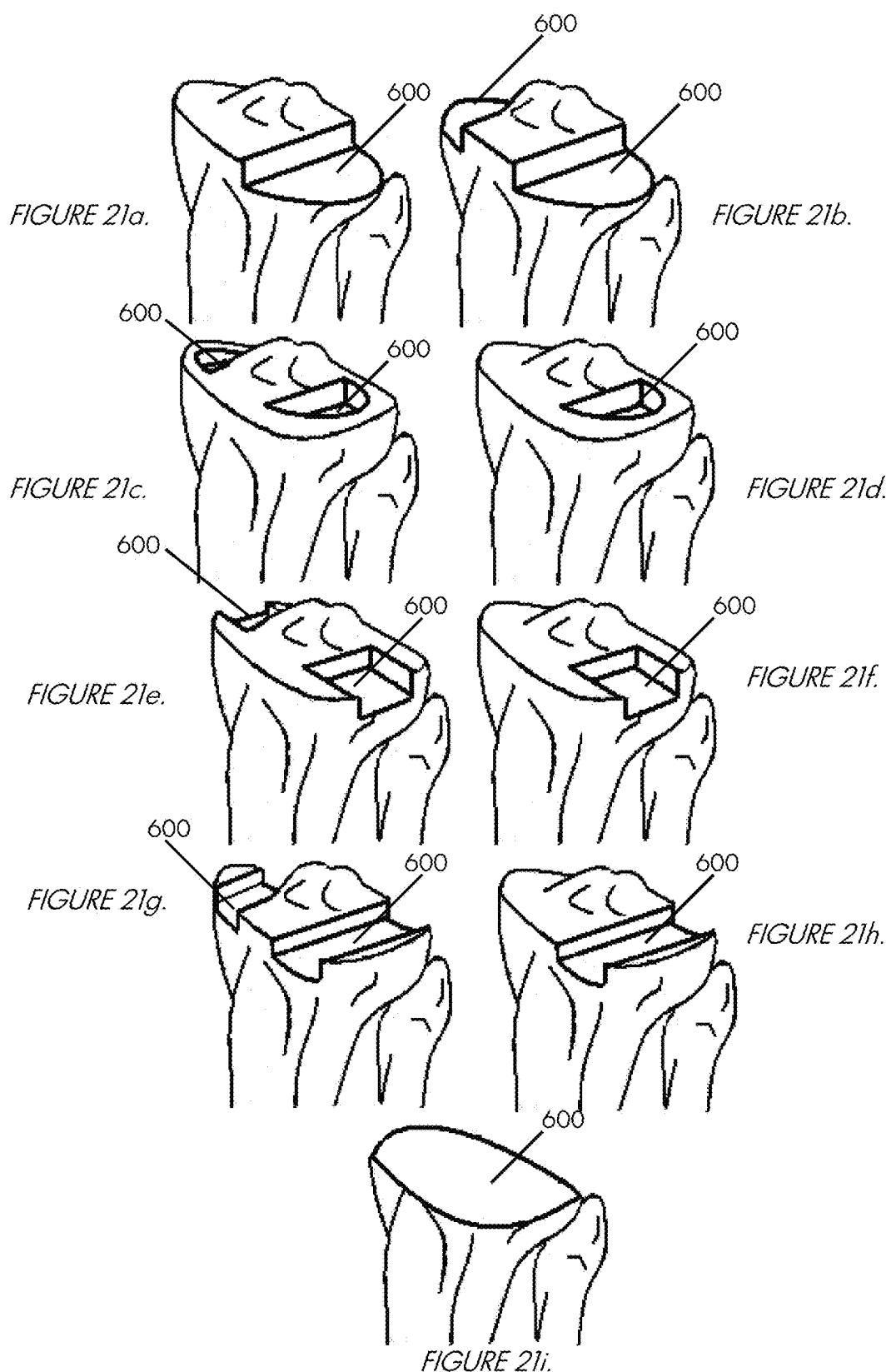
FIGS. 21a-21i illustrate several different bony resections achievable with the customized surgical device.

FIG. 20 shows an instance where more than one customized surgical devices (550,570) may be employed to create multiple bony resections (555,575) on a patient's limb, wherein each of said multiple bony resections (555,575) are perpendicular to the true, three-dimensional mechanical axis (590) of a patient's limb. In the instance show, a femoral resection (575) and tibial resection (555) is made, each being in a plane orthogonal to the true, three-dimensional mechanical axis of a patient's limb. This ensures that each portion of an installed knee prosthesis (i.e., femoral component, and tibial component(s)) will not experience excessive side shear forces which may eventually cause shifting, reduced ingrowth, cement degradation, pain, and reduced performance.

Figure 22:
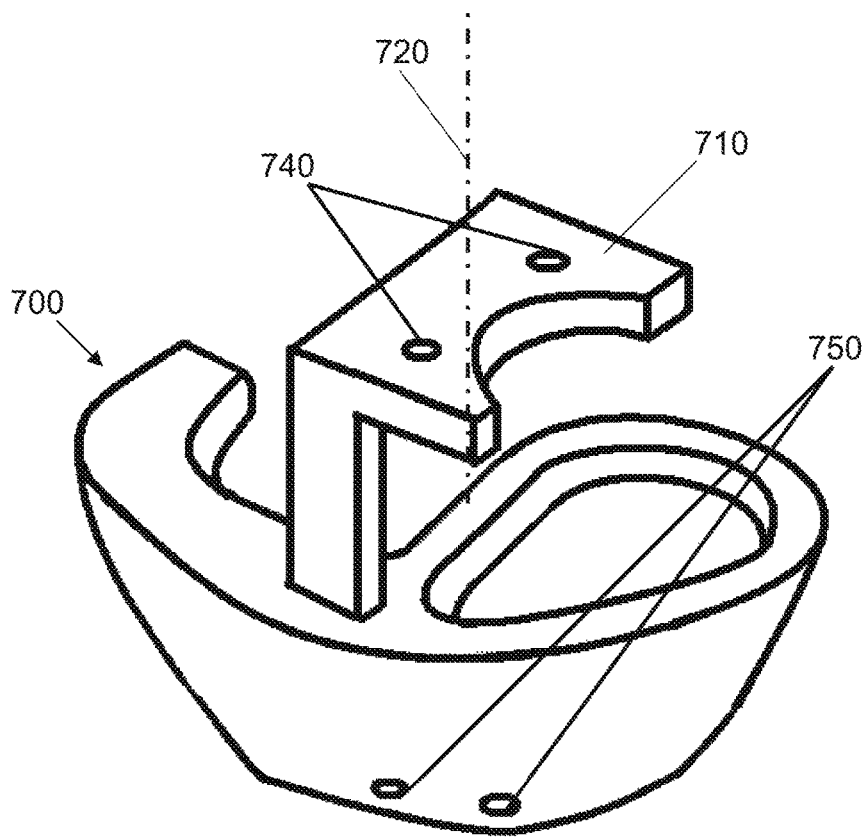
FIG. 22 illustrates an example of a customized surgical device configured to make a bony resection shown in FIG. 21d.

FIGS. 21a-21i illustrate some examples of bony resections. Each resection comprises at least one bony surface (600) which is perpendicular to the true, three dimensional mechanical axis of a limb. Preferably, the true, three-dimensional mechanical axis is a properly aligned, natural, or restored mechanical axis which is determined by one of the novel methods disclosed herein. FIG. 22 illustrates one non-limiting example of a customized surgical device (700) according some embodiments. The customized surgical device (700) generally conforms at least in part to a bony surface of a patient's limb, and is configured to create bony resections similar to the one shown in FIG. 21d. The device (700) has referencing means (710) for guiding a cutting tool perpendicular to the true, three-dimensional mechanical axis (720) of a particular patient's lower limb. Said cutting tool may comprise a mill, mill guide, router, or the like (not illustrated). Preferably, means for guiding a cutting tool (710) serves to establish a reference plane that is perpendicular to the true, three-dimensional mechanical axis (720) of a patient. Said means (710) may doubly serve as mounting means (740) for said cutting tool (not shown). Mounting means (750) may comprise without limitation: tongue-and-groove mechanisms, threaded holes, quarter turn fasteners, spring-locked detent fittings, or any other quick-connect/disconnect feature known in the coupling art. Stabilizing means (750) for mounting the customized surgical device (700) to a bony portion of a patient's limb may be utilized in order to prevent shifting under vibration from a cutting tool. Such stabilizing means (750) may comprise, for instance, oblique holes for holding pins (not shown). The customized surgical device (700) may comprise additional means for guiding a cutting tool, such as one or more cutting slots (not shown), in order to accommodate cutting tools of both the mill-type and blade-type.

Figure 23:
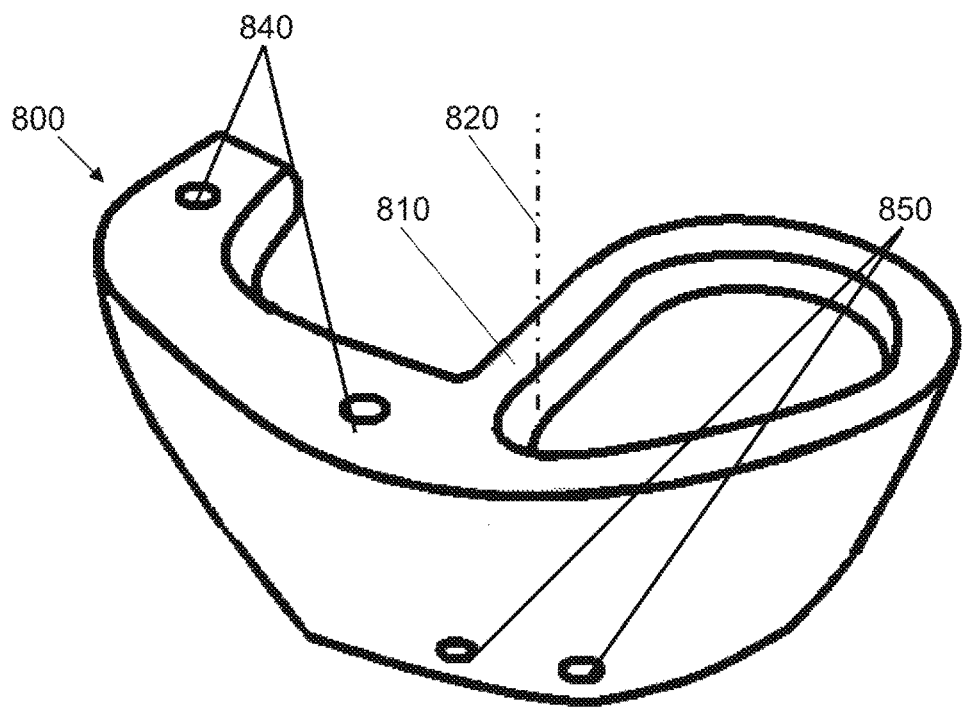
FIG. 23 illustrates another example of a customized surgical device configured to make a bony resection shown in FIG. 21d.

FIG. 23 shows a customized surgical device (800) alternative to the one shown in FIG. 22. The device (800) has referencing means (810) for guiding a cutting tool perpendicular to the true, three-dimensional mechanical axis (820) of a particular patient's lower limb. Said cutting tool may comprise a mill, mill guide, router, or the like (not illustrated). Preferably, means for guiding a cutting tool (810) serves to establish a reference plane that is perpendicular to the true, three-dimensional mechanical axis (820) of a patient. Said means (810) may doubly serve as mounting means (840) for said cutting tool (not shown). Mounting means (850) may comprise without limitation: tongue-and-groove mechanisms, threaded holes, quarter turn fasteners, spring-locked detent fittings, or any other quick-connect/disconnect feature known in the coupling art. Stabilizing means (850) for mounting the customized surgical device (800) to a bony portion of a patient's limb may also be utilized in order to prevent shifting under vibration from a cutting tool. Such stabilizing means (850) may comprise, for instance, oblique holes for holding pins (not shown). It should be under stood that the customized surgical device (800) may employ other means for guiding a cutting tool (810), such as a cutting slot (not shown) so as to accommodate other types of cutting tools, such as blades (not shown). The customized surgical device (800) may comprise additional means for guiding a cutting tool, such as one or more cutting slots (not shown), in order to accommodate cutting tools of both the mill-type and blade-type.

As various modifications could be made to the exemplary embodiments, as described above with reference to the corresponding illustrations, without departing from the scope, it is intended that all matter contained in the foregoing description and shown in the accompanying drawings shall be interpreted as illustrative rather than limiting. Thus, the breadth and scope should not be limited by any of the above-described exemplary embodiments, but should be defined only in accordance with the following claims appended hereto and their equivalents.

Figure 15:
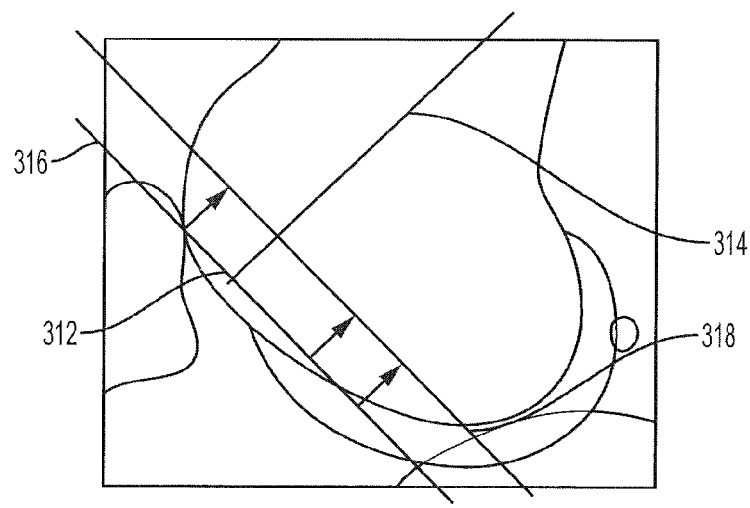
FIG. 15 shows alternative embodiments of distal resection depth.

There are many various exemplary embodiments which may be made and practiced. For instance, in some embodiments, it may be advantageous to provide a customized surgical device configured to provide a distal femoral resection (316) perpendicular to the true, three-dimensional mechanical axis (314) of a leg limb which passes through a distal sulcus point (312) of the intercondylar/trochlear groove as shown in FIG. 15. Or, it may be desirable to move said distal femoral resection (318) along said mechanical axis (314) so as to meet the needs of a patient. For instance, in younger patients, the bone stock may be good and a more conservative distal femoral resection (316) may be made. In other instances, such as older patients, or revision cases, a more aggressive, more proximally-located, distal femoral resection (318) may be made. In the case of revising a previous primary implant or prosthesis, a customized surgical device may be made to conform to previously-cut bone, a surface of the existing implant, or a combination thereof. The depth of any resection perpendicular to the true, three-dimensional mechanical axis may be determined by referencing from many different anatomical features. In some instances, a bony landmark on distal medial, distal lateral, or both distal medial and lateral condyle surfaces may determine the resection depth shown in FIG. 15. In other instances, resection depth may be determined by placing a resection line (318) a fixed predetermined distance from the cartilage/bone interface determined on a digital image (e.g., MR, CT, x-ray, fluoroscopic, ultrasound, other). In even other instances, a resection line (318) may be placed a fixed predetermined distance from a cortical/cancellous bone interface as determined on said digital image. In yet even other instances, a resection depth may be determined by offsetting the resection line (318) a predetermined distance from an anatomical landmark or feature. The anatomical landmark or feature may be a prominent feature easily visible in a digital image and is preferably generally consistent in its location between patients. Such anatomical landmarks may include any one or more of the following without limitation: epicondyles (32a,32b), trochlear sulcus (34), proximal tibia (48), prox fibula (52), patella (e.g., the inferior pole of the patella to be x mm from the joint line; x typically 2 cm or so), anterior cruciate ligament (ACL) insertion point, ACL length, posterior cruciate ligament (PCL) insertion point, PCL length, tibial tuberosity/tubercle (46), and others.

In other embodiments, non-invasive means such as computerized tomography may be used to determine the centroid of a femoral head and the midpoint of the transepicondylar axis. The true, three-dimensional mechanical axis may be accurately defined as the theoretical line connecting said centroid of the femoral head and said midpoint of the transepicondylar axis. A customized surgical device may then be provided, said customized surgical device being configured to guide a cutting tool along a plane generally perpendicular to said true, three-dimensional mechanical axis at a predetermined distance from said centroid of the femoral head and/or transepicondylar axis. Said plane may run through a distal sulcus point of the intercondylar/trochlear groove for maximum bone conservation, or may be positioned more proximal to the centroid of the femoral head to make room for a thicker implant or revision component.

Alternatively, the true, three-dimensional mechanical axis may be determined by using said non-invasive radiological means to determine the centroid of a femoral head and the transepicondylar axis of a distal femur. The transepicondylar axis may be found by locating at least first and second anatomical landmarks, said first and second anatomical landmarks being prominent portions of medial and lateral epicondyles, respectively. A theoretical line is projected from said centroid of the femoral head to said transepicondylar axis in such a way that the theoretical line intersects the transepicondylar axis at a right angle. Said theoretical line may generally be defined as the true, three-dimensional mechanical axis. A customized surgical device is then provided, said customized surgical device being configured to make at least one bony resection perpendicular to said true, three-dimensional mechanical axis.

Figure 16:
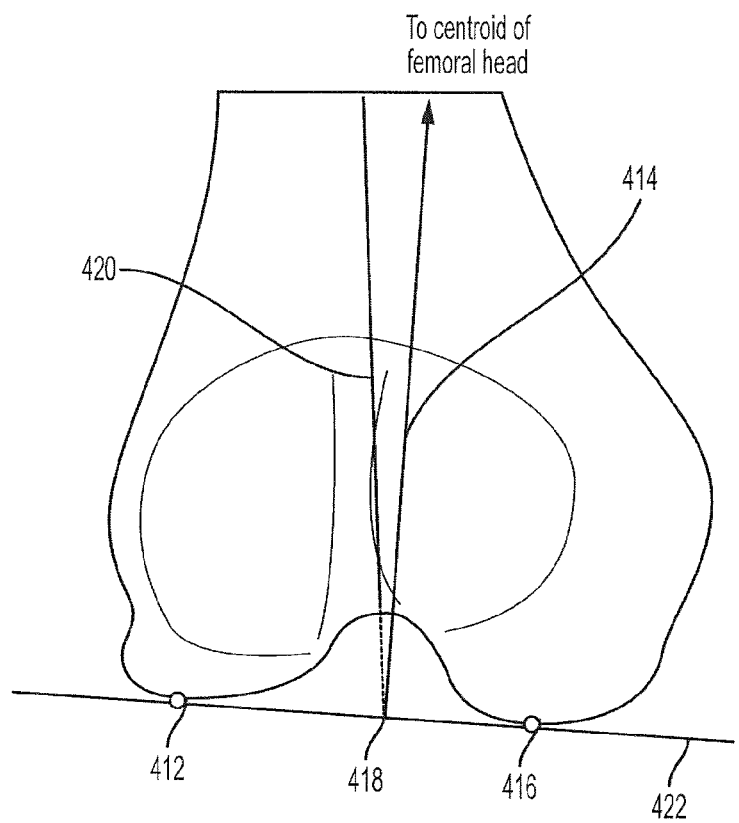
FIG. 16 illustrates a fifth method of determining a mechanical axis using non-invasive means.

As shown in FIG. 16, in some embodiments, a "virtual intramedullary rod" is created to determine the true, three-dimensional mechanical axis of a particular patient's limb. First, a partial proximal femur scan is taken, from which the centriod of the femoral head is located in space. Secondly, a partial scan of the knee joint is taken, from which the anatomical axis (420) of the distal femur is accurately determined. The anatomical axis (420) of the distal femur is projected distally in space (i.e. in a direction away from the femoral head), to a point in space between the distal medial and lateral condyles. The point in space (418) is preferably most adjacent a line (422) or a plane within a line connecting the distalmost portions of the medial (412) and lateral (416) condyles, respectively. The true, three-dimensional mechanical axis (414) may generally be defined as the imaginary line connecting said point in space (418) with the centroid of the femoral head (not illustrated). While said point in space (418) on the anatomical axis (420) may not always fall on said line (422) when projected, one of ordinary skill in the art could readily locate the point on the projected anatomical axis (420) which is closest in space to the line (422) to establish the point in space (418). A customized surgical device is then provided, said customized surgical device being configured to make at least one bony resection perpendicular to said true, three-dimensional mechanical axis (414).

Figure 17:
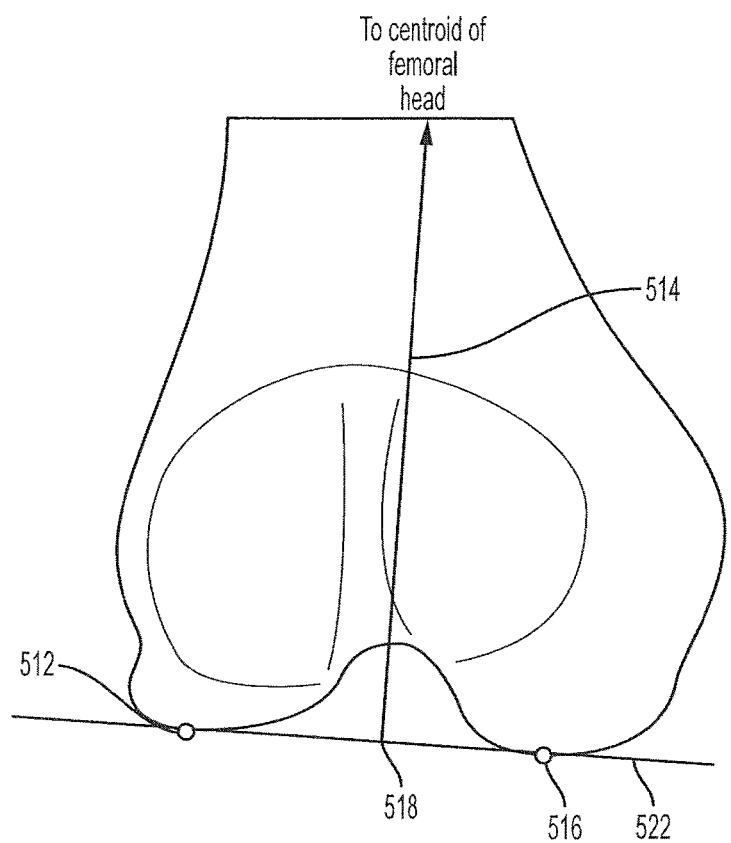
FIG. 17 illustrates a sixth method of determining a mechanical axis using non-invasive means.

Referring now, to FIG. 17, in some embodiments, the true, three-dimensional mechanical axis of a particular patient's limb may be determined by first generating a partial proximal femur scan, from which the centroid of the femoral head is located in space. Secondly, a partial scan of the knee joint is taken, from which the distalmost portions of the medial (512) and lateral (516) condyles are identified. A midpoint (518) is defined on a line (522) connecting the distalmost points on each of the medial (512) and lateral (516) condyles, respectively. The midpoint (518) is preferably centered in space between said distalmost points (512,516). The true, three-dimensional mechanical axis (514) may generally be defined as the imaginary line connecting said midpoint (518) with said centroid of the femoral head (not illustrated). A customized surgical device is then provided, said customized surgical device being configured to make at least one bony resection perpendicular to said true, three-dimensional mechanical axis.

Figure 24:
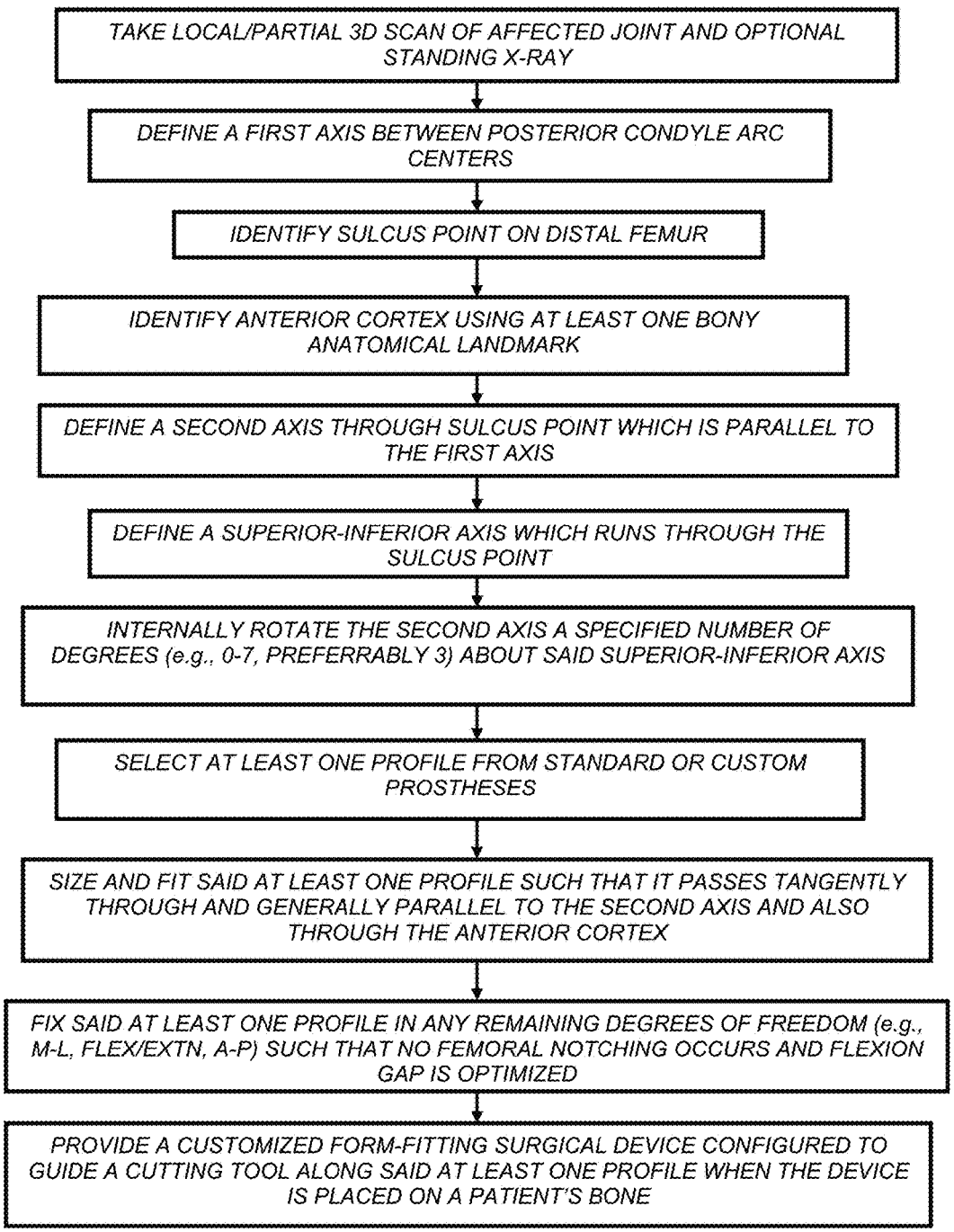
FIGS. 24-26 illustrate various method steps for providing a customized surgical device configured to make a bony resection perpendicular to the approximated true, three-dimensional mechanical axis of a patient's limb.
Figure 25:
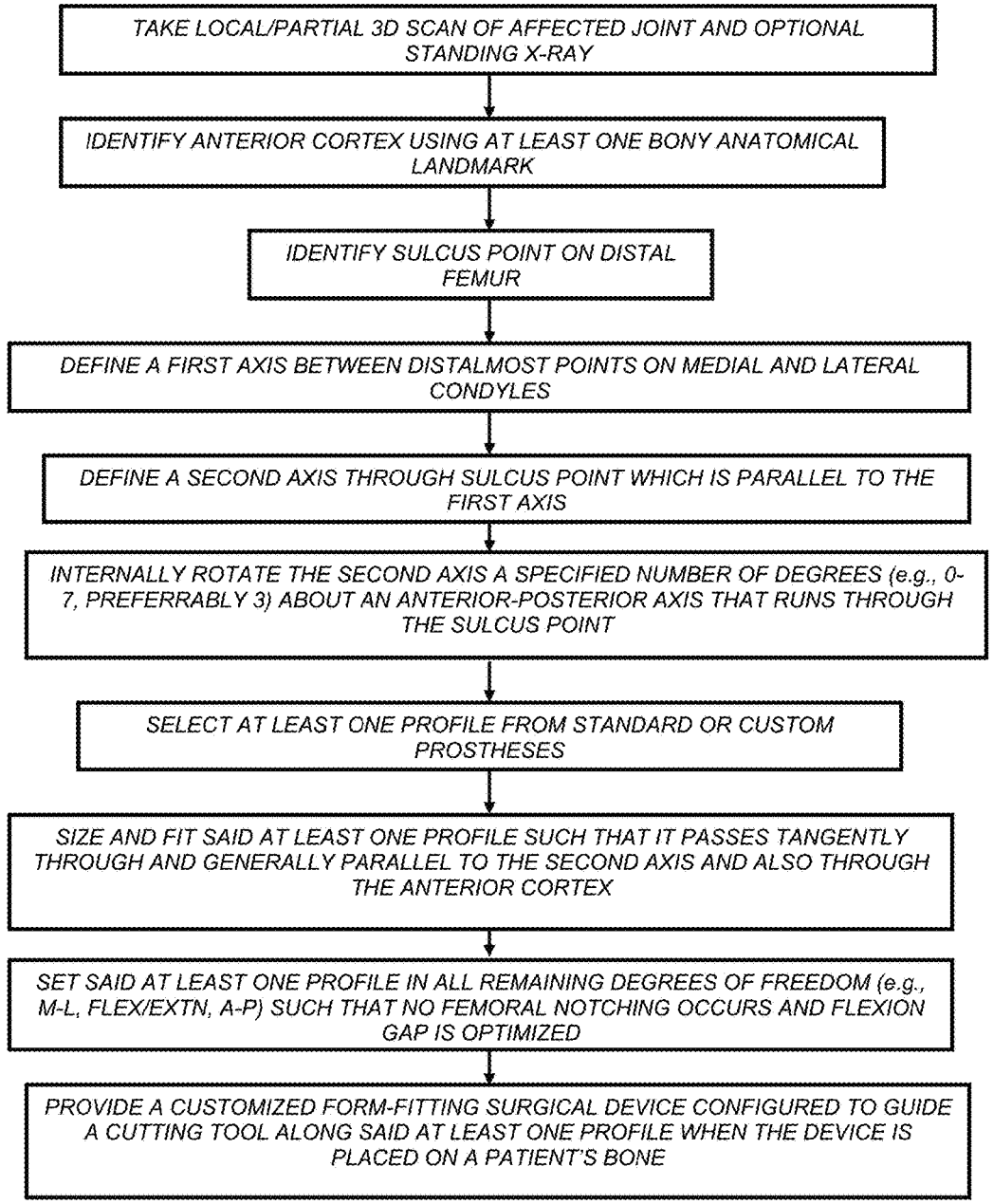
Figure 26:
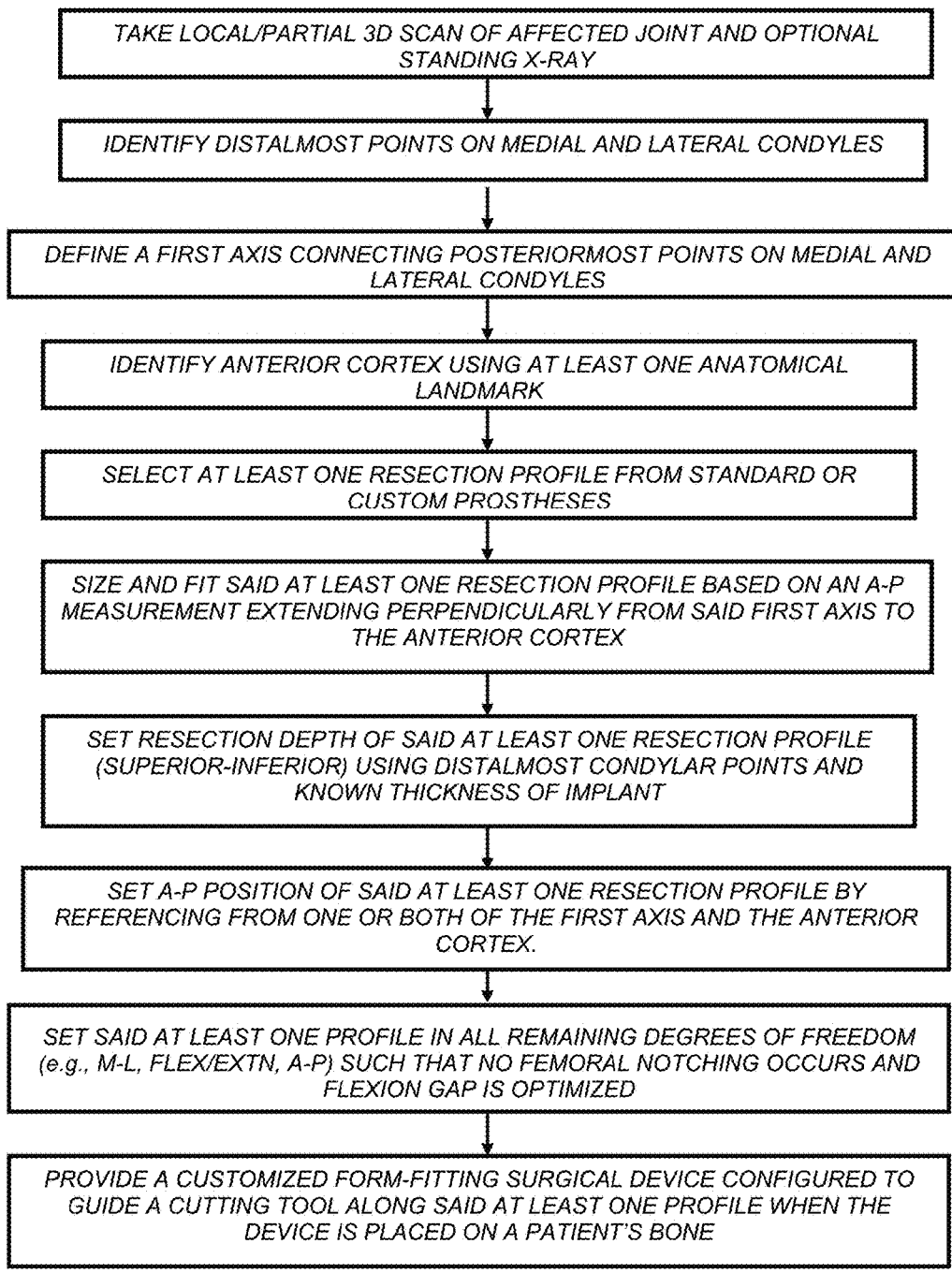

FIGS. 24-26 illustrate methods of providing a customized surgical device for a knee joint according to some embodiments. These methods may be advantageously utilized when only a partial 3D digital scan is available, when the true femoral head centre in space cannot be determined with computerized tomographical (CT) imaging, and/or when the transepicondylar axis may be compromised due to trauma or gross deformation.

Figure 27:
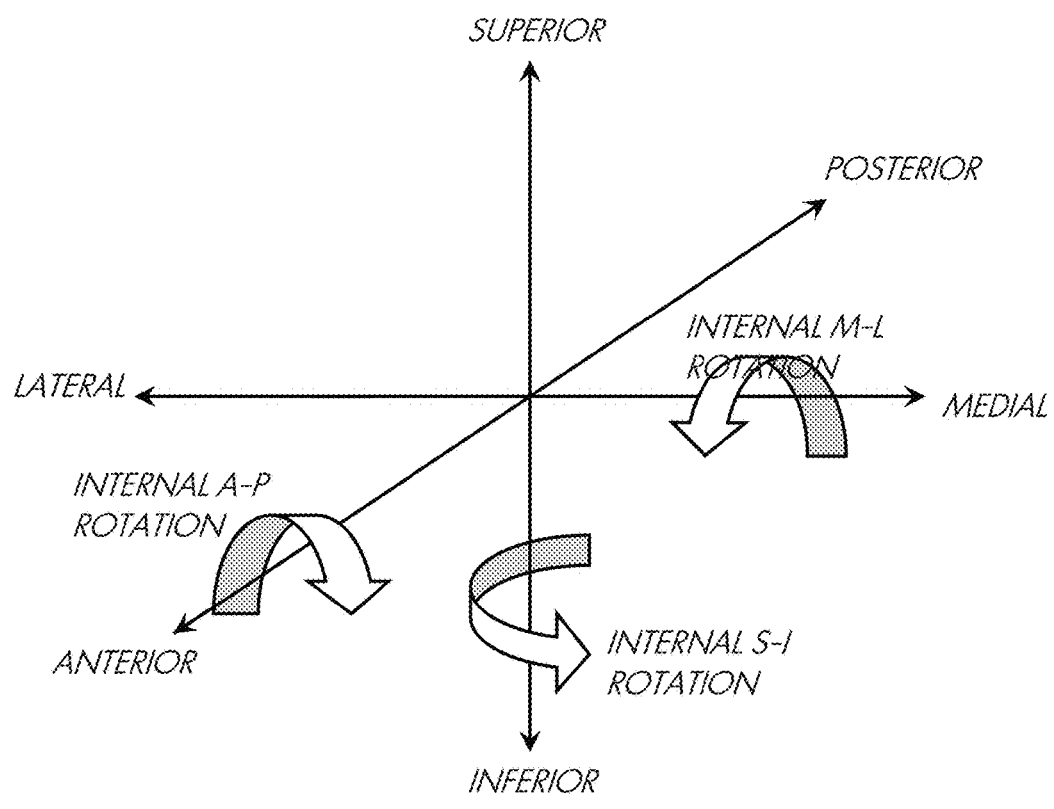
FIG. 27 illustrates a spatial reference coordinate system which may be used at any point on a limb or anatomical landmark of a limb.
Figures 28A, 28B:
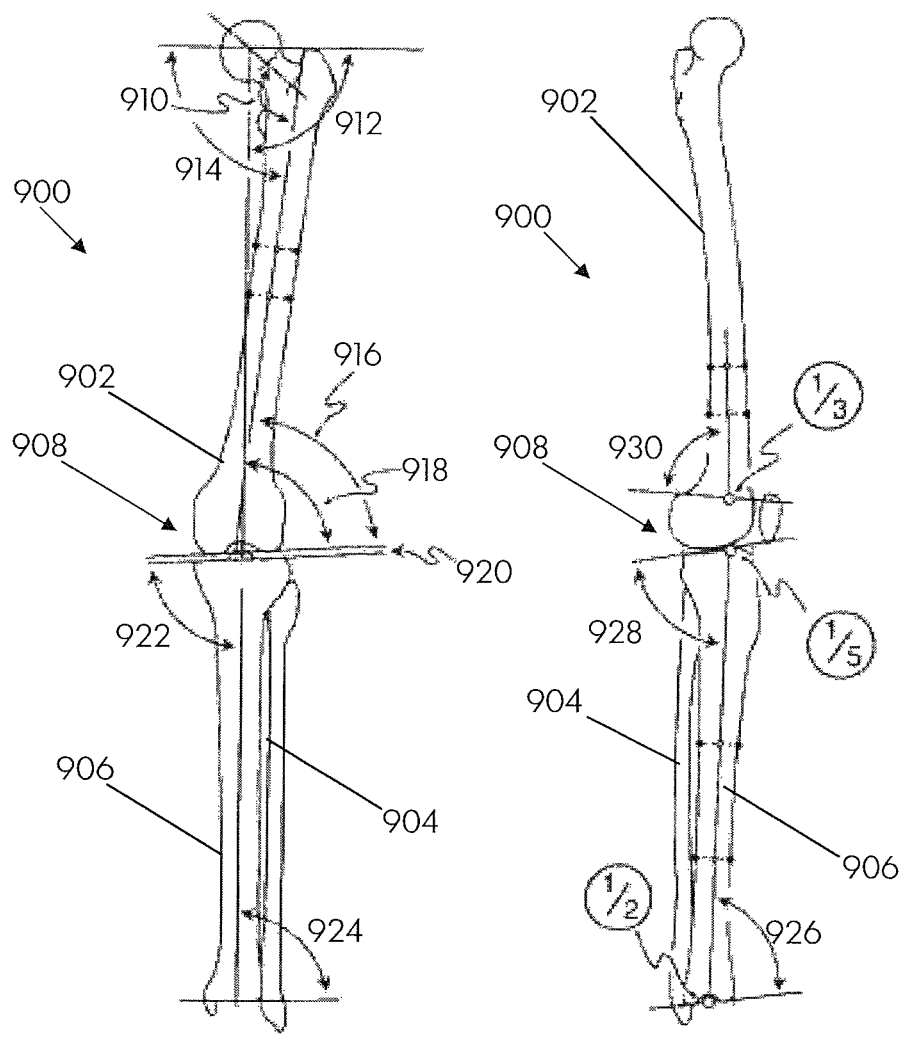
FIG. 28a shows a frontal view of a normal leg limb illustrating key relationships between anatomical features; and, FIG. 28b shows a sagittal view of a normal leg limb illustrating key relationships between anatomical features.

The method shown in FIG. 24 may be used in many situations; however, is particularly advantageous when: only a partial knee scan is available, the transepicondylar axis cannot be determined with accuracy, and/or the distal condyles are compromised. Using any means discussed herein, a partial 3D model of an affected knee joint of a patient is obtained. The posterior condyle arc-centres are found using computer software program, and a theoretical first line is created in space, said first line connecting the posterolateral condyle arc-centre and the posteromedial condyle arc-centre. A sulcus point within the trochlear groove on a distal portion of the femur is then identified. The sulcus point may generally be defined as a distal-most point within the intercondylar/trochlear groove, between the medial and lateral condyles. Next, the anterior cortex is identified. The anterior cortex may be generally defined as an anterior transitional portion on the distal femur. It may be necessary to identify one or more anatomical landmarks to best approximate the anterior cortex. It may also be necessary to determine the sulcus point using a reference coordinate system at the anterior cortex. This ensures that the sulcus point will be consistent for all angles of flexion and extension. Next, a theoretical second line is drawn in space through said sulcus point, said second line being generally parallel to said first line that connects posterior condyle arc-centres. A coordinate system having said sulcus point as an origin is defined. The coordinate system is generally shown in FIG. 27. The second line is internally rotated about the superior-inferior axis a predetermined number of degrees (i.e., internal S-I rotation). The predetermined number of degrees may vary between patients slightly, but is generally between zero and seven degrees, and preferably around three degrees. This predetermined number of degrees is generally consistent for patients with relatively normal anatomy and reflects a correction to approximate a line parallel with the transepicondylar axis. Next, at least one 3D or extruded 2D profile is selected from one or more standard prosthetic devices, or custom prosthetic devices. The at least one profile may be obtained from one or more product lines which may be from one or more implant manufacturers. Said at least one profile generally represents the bony resections (e.g., commonly termed "box" or "chamfered" cuts) needed to fit a particular standard or custom prosthetic device. After the at least one profile is selected, it may be superimposed on a 3D model of the affected joint bone, such that the profile passes tangently through said second line and anterior cortex. The at least one profile may be sized and fitted appropriately for best coverage, flexion gap stability, patella tracking, and placement without anterior femoral notching. If more than one profiles are utilized, a best choice on which profile (i.e., implant) to use may be made based on bone conservation tactics and other inputs. Once the at least one profile is set in all degrees of freedom, a customized surgical device may be created and provided. The customized surgical device preferably conforms in some way to a patient's bone and is generally specific to said patient. The bone-contacting surfaces of said customized surgical device may be large area surfaces having mirrored contours of a patient's bone thereon, or the bone-contacting surfaces may merely comprise a few specially-located contact points that lock said customized device in all degrees of freedom on said patient's bone. It is preferred, that like a key in a lock, the customized surgical device fits on a bony portion of a patient's affected limb in only one spatial orientation. The customized surgical device, as shown in FIGS. 18*a*-19*b*, may comprise one or more means for temporary bone fixation (562,564) to prevent movement under vibration caused by a cutting tool, and one or more means for guiding a cutting tool along said at least one profile. By following the above method steps, it is believed that at least one portion of the profile will be generally perpendicular to the true, three-dimensional mechanical axis of a patient's leg limb.

Similar to FIG. 24, FIG. 25 shows another method which may be advantageously used when only a partial knee scan is available, the transepicondylar axis cannot be determined with accuracy, and/or the posterior condyles are compromised. Using any means discussed herein, a partial 3D model of an affected knee joint of a patient is obtained. The distalmost points on each of the medial and lateral condyles are then found. The distalmost points may be determined through the use of a computer software program. Next, a theoretical first line is created in space, said first line connecting the distalmost point on the medial condyle and the distalmost point on the lateral condyle. A sulcus point within the trochlear groove on a distal portion of the femur is then identified. The sulcus point may generally be defined as a distal-most point within the intercondylar/trochlear groove, between the medial and lateral condyles. Next, the anterior cortex is identified. The anterior cortex may be generally defined as an anterior transitional portion on the distal femur. It may be necessary to identify one or more anatomical landmarks to best approximate the anterior cortex. It may also be necessary to determine the sulcus point using a reference coordinate system at the anterior cortex. This ensures that the sulcus point will be consistent for all angles of flexion and extension. Next, a theoretical second line is drawn in space through said sulcus point, said second line being generally parallel to said first line that connects the distalmost points on the medial and lateral condyles, respectively. A coordinate system having said sulcus point as an origin is defined. The coordinate system is generally shown in FIG. 27. The second line is externally rotated about the anterior-posterior axis a predetermined number of degrees (i.e., in a direction opposite internal a-p rotation) to compensate for a naturally-inclined joint line. The predetermined number of degrees may vary between patients slightly, but is generally between zero and seven degrees, and preferably around three degrees. This predetermined number of degrees is generally consistent for patients with relatively normal anatomy and reflects the relative relationship between a naturally-inclined joint line (about three degrees from horizontal) and the true, three-dimensional mechanical axis (about vertical). Next, at least one 3D or extruded 2D profile is selected from one or more standard prosthetic devices, or custom prosthetic devices. The at least one profile may be obtained from one or more product lines which may be from one or more implant manufacturers. Said at least one profile generally represents the bony resections (e.g., commonly termed "box" or "chamfered" cuts) needed to fit a particular standard or custom prosthetic device. After the at least one profile is selected, it may be superimposed on a 3D model of the affected joint bone, such that the profile passes tangently through said second line and anterior cortex. The at least one profile may be sized and fitted appropriately for best coverage, flexion gap stability, patella tracking, and placement without anterior femoral notching. If more than one profiles are utilized, a best choice on which profile (i.e., implant) to use may be made based on bone conservation tactics and other inputs. Once the at least one profile is set in all degrees of freedom, a customized surgical device may be created and provided. The customized surgical device preferably conforms in some way to a patient's bone and is generally specific to said patient. The bone-contacting surfaces of said customized surgical device may be large area surfaces having mirrored contours of a patient's bone thereon, or the bone-contacting surfaces may merely comprise a few specially-located contact points that lock said customized device in all degrees of freedom on said patient's bone. It is preferred, that like a key in a lock, the customized surgical device fits on a bony portion of a patient's affected limb in only one spatial orientation. The customized surgical device, as shown in FIGS. 18*a*-19*b*, may comprise one or more means for temporary bone fixation (562,564) to prevent movement under vibration caused by a cutting tool, and one or more means for guiding a cutting tool along said at least one profile. By following the above method steps, it is believed that at least one portion of the profile will be generally perpendicular to the true, three-dimensional mechanical axis of a patient's leg limb.

The method shown in FIG. 26 may be used when only a partial knee scan is available, the transepicondylar axis cannot be determined with accuracy, and the posterior condyle arc-centres cannot be determined with accuracy. Using any means discussed herein, a partial 3D model of an affected knee joint of a patient is obtained. The posteriormost and distalmost points on each of the medial and lateral condyles are then found. The points may be determined through the use of a computer software program. Next, a theoretical first line is created in space, said first line connecting the posteriormost point on the medial condyle and the posteriormost point on the lateral condyle. A sulcus point within the trochlear groove on a distal portion of the femur is also identified. The sulcus point may generally be defined as a distal-most point within the intercondylar/trochlear groove, between the medial and lateral condyles. Next, the anterior cortex is identified. The anterior cortex may be generally defined as an anterior transitional portion on the distal femur. It may be necessary to identify one or more anatomical landmarks to best approximate the anterior cortex. It may also be necessary to determine the sulcus point using a reference coordinate system at the anterior cortex. This ensures that the sulcus point will be consistent for all angles of flexion and extension. Next, at least one 3D or extruded 2D profile is selected from one or more standard prosthetic devices, or custom prosthetic devices. The at least one profile may be obtained from one or more product lines which may be from one or more implant manufacturers. Said at least one profile generally represents the bony resections (e.g., commonly termed "box" or "chamfered" cuts) needed to fit a particular standard or custom prosthetic device. After the at least one profile is selected, it may be superimposed on a 3D model of the affected joint bone and sized. Sizing is performed by taking a perpendicular measurement from said first line to the anterior cortex. In the instance of non-standard prosthetic devices, a particular patient may be in-between sizes. In these cases, said profile may be positioned anteriorly-posteriorly by posterior referencing, anterior referencing, or a combination thereof. If posterior referencing, the A-P positioning of the profile will be set such that the posteriormost points on medial and lateral condylar bearing surfaces of a selected femoral implant will be adjacent to or intersect the posteriormost points on the patient's natural bone. If anterior-referencing is preferred, the A-P positioning of the profile will be set such that an anterior portion of the profile intersects the anterior cortex without notching the femur. A combination of these two methods may be utilized to find a good compromise between optimal patella tracking and restoring pre-operative joint biomechanics in deep flexion. In any event, however, the profile is aligned so as to have all cuts be generally parallel to the first line connecting the posterior condyles. Profile depth is then assessed from the two distalmost points on the medial and lateral condyles. The profile is moved superiorly-inferiorly along the femur and set at a distance approximating an implant thickness from said distalmost points on medial and lateral condyles. All remaining degrees-of-freedom (M/L, Flexion/extension) are set such that femoral notching does not occur and flexion gap is optimized. The at least one profile may be sized and fitted appropriately for best coverage, flexion gap stability, patella tracking, and placement without anterior femoral notching. If more than one profiles are used in computer-aided "virtual trialling", a best choice on which profile (i.e., implant) to use may be made based on bone conservation tactics and other inputs. Once the at least one profile is set in all degrees of freedom, a customized surgical device may be created and provided. The customized surgical device preferably conforms in some way to a patient's bone and is generally specific to said patient. The bone-contacting surfaces of said customized surgical device may be large area surfaces having mirrored contours of a patient's bone thereon, or the bone-contacting surfaces may merely comprise a few specially-located contact points that lock said customized device in all degrees of freedom on said patient's bone. It is preferred, that like a key in a lock, the customized surgical device fits on a bony portion of a patient's affected limb in only one spatial orientation. The customized surgical device, as shown in FIGS. 18a-19b, may comprise one or more means for temporary bone fixation (562,564) to prevent movement under vibration caused by a cutting tool, and one or more means for guiding a cutting tool along said at least one profile. By following the above method steps, it is believed that at least one portion of the profile will be generally perpendicular to the true, three-dimensional mechanical axis of a patient's leg limb.

All of the above methods illustrated in FIGS. 24-26 may optionally employ computer Aided Design (CAD) programs and Finite Element Analysis (FEA) software may be incorporated to virtually test a given implant's performance. For instance, once a profile is fixed in space on a 3D model of a patient's limb, an implant having the same profile as a bony interface may be superimposed on the 3D model. Software may perform iterative test runs to predict whether or not small adjustments to the positioning of the profile are necessary to optimize performance.

The aforementioned embodiments as well as the appended drawings are illustrative in nature and in no way limit or define the invention. The method steps as disclosed may be practiced in any order.

The method improves over prior methods of providing customized surgical devices, because it is believed that current methods of customizing surgical devices do not include the step of accurately determining the true, three-dimensional mechanical axis of a patient's limb. Instead, it is believed that prior art methods reference all bony cuts from the anatomical axis, particularly, from an anatomical axis defined from only a partial scan of the knee joint. The prior art "assumes" a mechanical axis that is located at a predetermined angle medially from the anatomical axis. This method is believed to be deficient, because it does not take into consideration uniqueness of anatomy between patients (which ranges from 2-11 degrees as previously discussed). The methods of the prior art are also deemed to be inefficient and inaccurate, because they rely wholly on generalized observations for a large population set. The method may ensure that for each unique patient, the true, three-dimensional mechanical axis for that patient is determined, and that at least one bony resection of a limb of said patient is made perpendicular to said true, three-dimensional mechanical axis to avoid side shear stresses on an implant. In doing so, an implant is loaded in compression in one axis only (i.e., along the mechanical axis) and is less likely to experience side shear stresses. Excessive side shear stresses on an implant when under load may increase wear rate, cause loosening, fracture cement at the bony interface, risk soft tissue impingement, decrease performance, and cause pain.

In view of the foregoing, it will be seen that the several advantages of the invention are achieved and attained.

The embodiments were chosen and described in order to best explain the principles of the invention and its practical application to thereby enable others skilled in the art to best utilize the invention in various embodiments and with various modifications as are suited to the particular use contemplated.

As various modifications could be made in the constructions and methods herein described and illustrated without departing from the scope of the invention, it is intended that all matter contained in the foregoing description or shown in the accompanying drawings shall be interpreted as illustrative rather than limiting. Thus, the breadth and scope of the present invention should not be limited by any of the above-described exemplary embodiments, but should be defined only in accordance with the following claims appended hereto and their equivalents.

What is claimed is:

1. A method comprising:
obtaining patient-specific anatomical data of a limb;
identifying a plurality of anatomical landmarks of the limb using the patient-specific anatomical data;
performing a series of computations to determine a three-dimensional mechanical axis of the limb based on the identified plurality of anatomical landmarks;
determining one or more planes for bone cuts on the limb based on the identified plurality of landmarks and the determined three-dimensional mechanical axis of the limb, at least one of the one or more planes having a predetermined orientation with respect to the determined three-dimensional mechanical axis of the limb; and
manufacturing a patient-specific surgical item based at least partially on the determined three-dimensional mechanical axis of the limb, the patient-specific surgical item including a portion that conforms to a corresponding portion of a bony surface of the limb such that the patient-specific surgical item is configured to engage the limb in a predetermined orientation, and the patient-specific surgical item is configured to indicate the determined one or more planes with respect to the limb when the patient-specific surgical item is engaged with the limb in the predetermined orientation.

2. The method of claim 1, wherein performing a series of computations to determine the three-dimensional mechanical axis of the limb based on the identified plurality of anatomical landmarks comprises iteratively identifying spatial relationships or constraints to define the three-dimensional mechanical axis of the limb.

3. The method of claim 1, wherein performing a series of computations to determine the three-dimensional mechanical axis of the limb based on the identified plurality of anatomical landmarks comprises performing multiple computations that are each based on locations of different anatomical landmarks of the plurality of anatomical landmarks.

4. The method of claim 1, wherein determining the one or more planes for bone cuts on the limb comprises determining one or more planes for bone cuts to prepare the limb to receive a particular prosthetic component in a particular size.

5. The method of claim 1, wherein determining the one or more planes for bone cuts on the limb comprises determining multiple planes for chamfered cuts on a femur.

6. The method of claim 1, wherein determining the one or more planes for bone cuts on the limb comprises determining one or more planes for cuts on a tibia.

7. The method of claim 1, further comprising determining a position for a prosthetic component with respect to a three-dimensional model of the limb such that the prosthetic component has a predetermined orientation with respect to the determined mechanical axis of the limb.

8. The method of claim 1, wherein manufacturing the patient-specific surgical item comprises manufacturing a patient-specific cutting block having one or more guide elements configured to guide a resection along the determined one or more planes.

9. The method of claim 8, wherein each of the one or more guide elements comprises a planar cutting surface or a cutting slot.

10. The method of claim 1, wherein identifying the plurality of anatomical landmarks comprises identifying a tibial intercondylar eminence of the limb.

11. The method of claim 1, wherein determining the one or more planes for bone cuts comprises:
establishing positions of the one or more planes in all but 2 degrees of freedom; and
after establishing the positions of the one or more planes in all but 2 degrees of freedom, further constraining the positions of the one or more planes to establish an appropriate flexion gap for a joint of the limb.

12. A method comprising:
obtaining patient-specific anatomical data of a limb;
identifying a plurality of anatomical landmarks of the limb using the patient-specific anatomical data;
determining, based on the identified plurality of anatomical landmarks, a position of a prosthetic component such that the prosthetic component has a predetermined orientation with respect to a mechanical axis of the limb; and
determining one or more planes for bone cuts on the limb based on the determined position of the prosthetic component, at least one of the one or more planes having a predetermined orientation with respect to the mechanical axis of the limb, wherein determining the one or more planes for bone cuts on the limb comprises iteratively changing positions of the one or more planes.

13. The method of claim 12, wherein determining the position of the prosthetic component comprises adjusting a position of a profile of a three-dimensional computer model of the prosthetic component with respect to a three-dimensional computer model of the limb determined based on imaging data for the limb; and
wherein determining the one or more planes for bone cuts on the limb comprises determining one or more planes along the profile of the three-dimensional computer model of the prosthetic component after adjusting the position of the profile.

14. The method of claim 13, wherein adjusting the position of the profile of the three-dimensional computer model of the prosthetic component comprises adjusting the position of the profile to adjust a flexion gap for a joint of the limb.

15. The method of claim 13, wherein determining the position of the prosthetic component comprises determining an anterior-posterior positioning for the prosthetic component such that posterior-most portions of medial and lateral condylar bearing surfaces of a femoral implant are adjacent to or intersect posterior-most portions of natural bone of the limb.

16. A method comprising:
obtaining patient-specific anatomical data of a limb;
identifying a plurality of anatomical landmarks of the limb using the patient-specific anatomical data;
performing a series of computations to determine a three-dimensional mechanical axis of the limb based on the identified plurality of anatomical landmarks, wherein performing the series of computations comprises performing multiple computations that are each based on locations of different anatomical landmarks of the plurality of anatomical landmarks; and
determining one or more planes for bone cuts on the limb based on the identified plurality of landmarks and the determined three-dimensional mechanical axis of the limb, at least one of the one or more planes having a predetermined orientation with respect to the determined three-dimensional mechanical axis of the limb.

17. The method of claim 16, wherein obtaining the patient-specific anatomical data comprises obtaining pre-operative imaging data for the limb that indicates contours of at least one bone of the limb;
wherein identifying the plurality of anatomical landmarks comprises identifying the plurality of anatomical landmarks with respect to a digital three-dimensional model of one or more bones of the limb generated based on pre-operative imaging data for the limb;
wherein determining the one or more planes for bone cuts on the limb comprises determining a position of a digital three-dimensional model of a prosthetic component with respect to the digital three-dimensional model of one or more bones of the limb and determining the one or more planes based on the determined position of the digital three-dimensional model of the prosthetic component; and
wherein the method further comprises manufacturing a patient-specific cutting guide including a portion that conforms to a corresponding portion of a bony surface of the limb such that the patient-specific surgical item is configured to engage the bony surface of the limb in a predetermined orientation, the patient-specific cutting guide being configured to indicate the determined one or more planes with respect to the limb when the patient-specific surgical item is engaged with the bony surface of the limb in the predetermined orientation.

18. A method comprising:
obtaining patient-specific anatomical data of a limb;
identifying a plurality of anatomical landmarks of the limb using the patient-specific anatomical data, wherein identifying the plurality of anatomical landmarks comprises identifying a tibial intercondylar eminence of the limb;
performing a series of computations to determine a three-dimensional mechanical axis of the limb based on the identified plurality of anatomical landmarks; and
determining one or more planes for bone cuts on the limb based on the identified plurality of landmarks and the determined three-dimensional mechanical axis of the limb, at least one of the one or more planes having a predetermined orientation with respect to the determined three-dimensional mechanical axis of the limb.

19. The method of claim 18, wherein obtaining the patient-specific anatomical data comprises obtaining pre-operative imaging data for the limb that indicates contours of at least one bone of the limb;
wherein identifying the plurality of anatomical landmarks comprises identifying the plurality of anatomical landmarks with respect to a digital three-dimensional model of one or more bones of the limb generated based on pre-operative imaging data for the limb;
wherein determining the one or more planes for bone cuts on the limb comprises determining a position of a digital three-dimensional model of a prosthetic component with respect to the digital three-dimensional model of one or more bones of the limb and determining the one or more planes based on the determined position of the digital three-dimensional model of the prosthetic component; and
wherein the method further comprises manufacturing a patient-specific cutting guide including a portion that conforms to a corresponding portion of a bony surface of the limb such that the patient-specific surgical item is configured to engage the bony surface of the limb in a predetermined orientation, the patient-specific cutting guide being configured to indicate the determined one or more planes with respect to the limb when the patient-specific surgical item is engaged with the bony surface of the limb in the predetermined orientation.

20. A method comprising:
obtaining patient-specific anatomical data of a limb;
identifying a plurality of anatomical landmarks of the limb using the patient-specific anatomical data, wherein identifying the plurality of anatomical landmarks comprises identifying a tibial intercondylar eminence of the limb;
performing a series of computations to determine a three-dimensional mechanical axis of the limb based on the identified plurality of anatomical landmarks; and
determining one or more planes for bone cuts on the limb based on the identified plurality of landmarks and the determined three-dimensional mechanical axis of the limb, at least one of the one or more planes having a predetermined orientation with respect to the determined three-dimensional mechanical axis of the limb, wherein determining the one or more planes for bone cuts comprises:
establishing positions of the one or more planes in all but 2 degrees of freedom; and
after establishing the positions of the one or more planes in all but 2 degrees of freedom, further constraining the positions of the one or more planes to establish an appropriate flexion gap for a joint of the limb.

21. The method of claim 20, wherein obtaining the patient-specific anatomical data comprises obtaining pre-operative imaging data for the limb that indicates contours of at least one bone of the limb;
wherein identifying the plurality of anatomical landmarks comprises identifying the plurality of anatomical landmarks with respect to a digital three-dimensional model of one or more bones of the limb generated based on pre-operative imaging data for the limb;
wherein determining the one or more planes for bone cuts on the limb comprises determining a position of a digital three-dimensional model of a prosthetic component with respect to the digital three-dimensional model of one or more bones of the limb and determining the one or more planes based on the determined position of the digital three-dimensional model of the prosthetic component; and
wherein the method further comprises manufacturing a patient-specific cutting guide including a portion that conforms to a corresponding portion of a bony surface of the limb such that the patient-specific surgical item is configured to engage the bony surface of the limb in a predetermined orientation, the patient-specific cutting guide being configured to indicate the determined one or more planes with respect to the limb when the patient-specific surgical item is engaged with the bony surface of the limb in the predetermined orientation.

22. A method comprising:
obtaining patient-specific anatomical data of a limb;
identifying a plurality of anatomical landmarks of the limb using the patient-specific anatomical data;
determining, based on the identified plurality of anatomical landmarks, a position of a prosthetic component such that the prosthetic component has a predetermined orientation with respect to a mechanical axis of the limb, wherein determining the position of the prosthetic component comprises adjusting a position of a profile of a three-dimensional computer model of the prosthetic component with respect to a three-dimensional computer model of the limb determined based on imaging data for the limb, wherein adjusting the position of the profile of the three-dimensional computer model of the prosthetic component comprises adjusting the position of the profile to adjust a flexion gap for a joint of the limb; and
determining one or more planes for bone cuts on the limb based on the determined position of the prosthetic component, at least one of the one or more planes having a predetermined orientation with respect to the mechanical axis of the limb, wherein determining the one or more planes for bone cuts on the limb comprises determining one or more planes along the profile of the three-dimensional computer model of the prosthetic component after adjusting the position of the profile.

23. The method of claim 22, further comprising manufacturing a patient-specific cutting guide including a portion that conforms to a corresponding portion of a bony surface of the limb such that the patient-specific surgical item is configured to engage the bony surface of the limb in a predetermined orientation, the patient-specific cutting guide being configured to indicate the determined one or more planes with respect to the limb when the patient-specific surgical item is engaged with the bony surface of the limb in the predetermined orientation.

24. The method of claim 1, wherein determining the one or more planes for bone cuts on the limb comprises iteratively changing positions of the one or more planes.

* * * * *